United States Patent [19]
Tedder

[11] Patent Number: 5,831,142
[45] Date of Patent: Nov. 3, 1998

[54] REGULATORY ELEMENTS CONTROLLING TISSUE-SPECIFIC GENE EXPRESSION

[75] Inventor: Thomas F. Tedder, Durham, N.C.

[73] Assignee: Dana Farber Cancer Institute, Inc., Boston, Mass.

[21] Appl. No.: 179,626

[22] Filed: Jan. 7, 1994

[51] Int. Cl.$^6$ .................................................. C12N 15/00
[52] U.S. Cl. ........................................ 800/2; 800/DIG. 1
[58] Field of Search .................................. 800/2, DIG. 1; 435/240.2, 320.1; 536/23.1, 23.5, 24.1

[56] References Cited

PUBLICATIONS

JE Maguire et al (1992) Molecular and Cellular Biology 12: 3078–3086.
Riegman et al (1991) Molecular Endocrinology 5: 1921–1930.
Zhou et al (1993) 5$^{th}$ International Conference on Human Leukocyte Differentiation Antigens, Abstract B117 Kozmik et al (1992) Mol Cell Biol 12: 2662–2672.
Watson et al (1987) Molecular Biology of the Gene, p. 313.
Volanakis et al., "Major Histocompatibility Complex Class III Genes and Susceptibility to Immunoglobulin A Deficiency and Common Variable Immunodeficiency", 1992, J. Clin. Invest. 89:1914–1922.
Olerup et al., "Shared HLA class II–associated Genetic Susceptibility and Resistance, Related to the HLA–DQB1 Gene, in IgA Deficiency and Common Variable Immunodeficiency", 1992, Proc. Natl. Acad. Sci. USA 89:10653–10657.
Mori et al., "Diversity in DNA Rearrangements and in RNA Expressions of Immunoglobulin Gene on Common Variable Immunodeficiency", 1992, Europ. J. of Immunogenetics 19:273–285.
Storb et al., "High Expression of Cloned Immunoglobulin κ Gene in Transgenic Mice is Restricted to B Lymphocytes", 1984, Nature 310;228–241.
Zhou et al., "Structure of the Genes Encoding the CD19 Antigen os Human and Mouse B Lymphocytes", 1992, Immunogenetics 35:102–111.
Zhou et al., "Structure and Domain Organization of hte CD19 Antigen of Human, Mouse, and Guinea Pig B Lymphocytes", 1991, The Journal of Immunology 147:1424–1432.
Alexander et al., "Expression of the c–myc Oncogene Under Control of an Immunoglobulin Enhancer in Eμ–myc Transgene Mice", 1987, Molecular and Cellular Biology 7:1436–1444.

Tsukada et al., "Deficient Expression of a B Cell Cytoplasmic Tyrosine Kinase in Human X–Linked Agammaglobulinemia", 1993, Cell 72:279–290.
Abraham et al., "Delayed Thymocyte Development Induced by Augmented Expression of p56$^{lck}$", 1991, J. Exp. Med. 173:1421–1432.
Klinken et al., "Hemopoietic Lineage Switch: v–raf Oncogene Converts Eμ–myc Transgenic B Cells into Macrophages", 1988, Cell 53:857–867,.
Rogerson et al., "Mutation Pattern of Immunoglobulin Transgenes is Compatible with a Model of Somatic Hypermutation in which Targeting of the Mutator is Linked to the Direction of DNA Replication", 1991, The EMBO Journal 10:4331–4341.
Era et al., "Differentiation of Growth Signal Requirement of B Lymphocyte Precursor is Directed by Expression of Immunoglobulin", 1991, The EMBO Journal 10:337–342.
Muller et al., "Membrane–Bound IgM Obstructs B Cell Development in Transgenic Mice", 1989, Euro. J. Immunol. 19:923–928.
Shimizu et al., "Synthesis and Regulation of trans –mRNA Encoding the Immunoglobulin ε Heavy Chain", 1993, The FASEB Journal 7:149–154.
Sidman et al., "Multiple Mechanisms of Tumorigenesis in Eμ–myc Transgenic Mice", 1993, Cancer Research 53:1665–1669.
Moroy et al., "IgH Enhancer Deregulated Expression of L–myc : Abnormal T Lymphocyte Development and T Cell Lymphomeasgenesis", 1990, The EMBO Journal 9:3659–3666.
Levin et al., "A Dominant–Negative Transgene Defines a Role for p56$^{lck}$ in Thymopoiesis", 1993, The EMBO Journal 12:1671–1680.
Herzenburg et al., "Depletion of the Predominant B–cell Population in Immunoglobulin μ Heavy–Chain Transgenic Mice", 1987, Nature 329:71–73.
Barberis et al., "A Novel B–Cell Lineage–Specific Transcription Factor Present at Early But Not Late Stages of Differentiation", 1990, Genes & Development 4:849–859.
Thomas et al., "Colocalization of X–linked Agammaglobulinemia and X–linked Immunodeficiency Genes", 1993, Science 261:355–358.

*Primary Examiner*—Bruce R. Campbell
*Attorney, Agent, or Firm*—Weingarten, Schurgin, Gagnebin & Hayes LLP

[57] ABSTRACT

The invention includes recombinant DNA regulatory elements which control expression of the CD19 gene in a B-lineage-restricted manner.

1 Claim, 16 Drawing Sheets

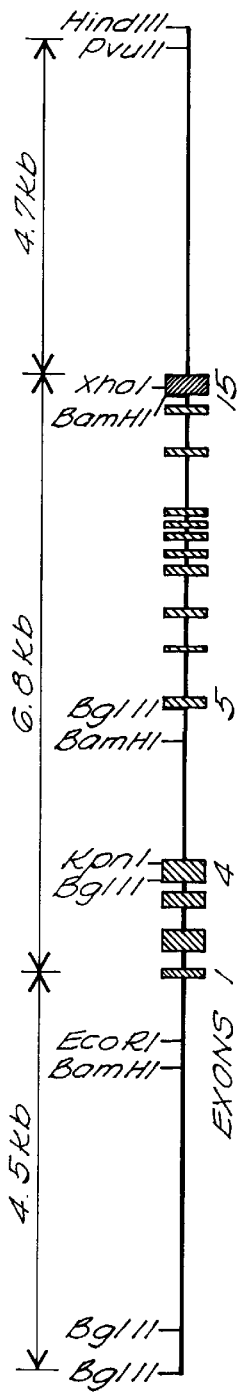

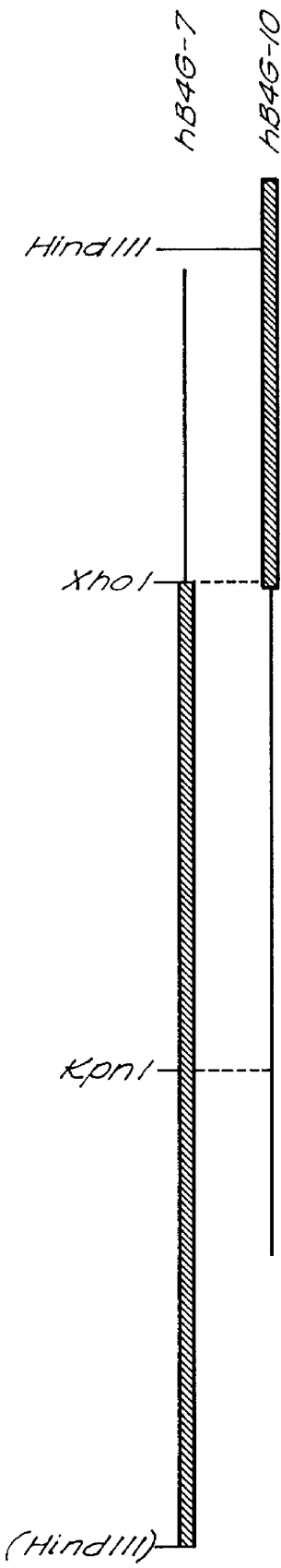
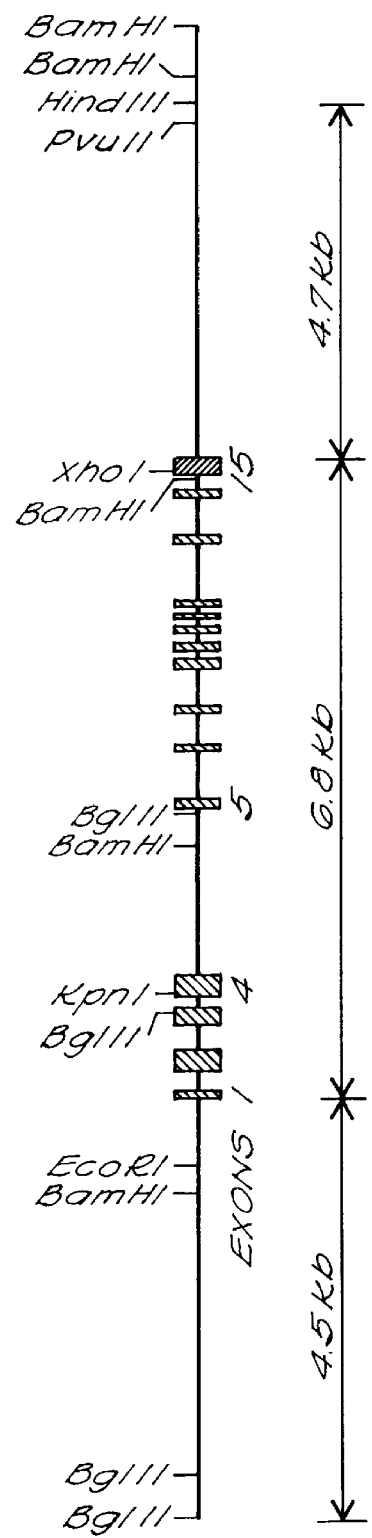
FIG. 4A
FIG. 4B

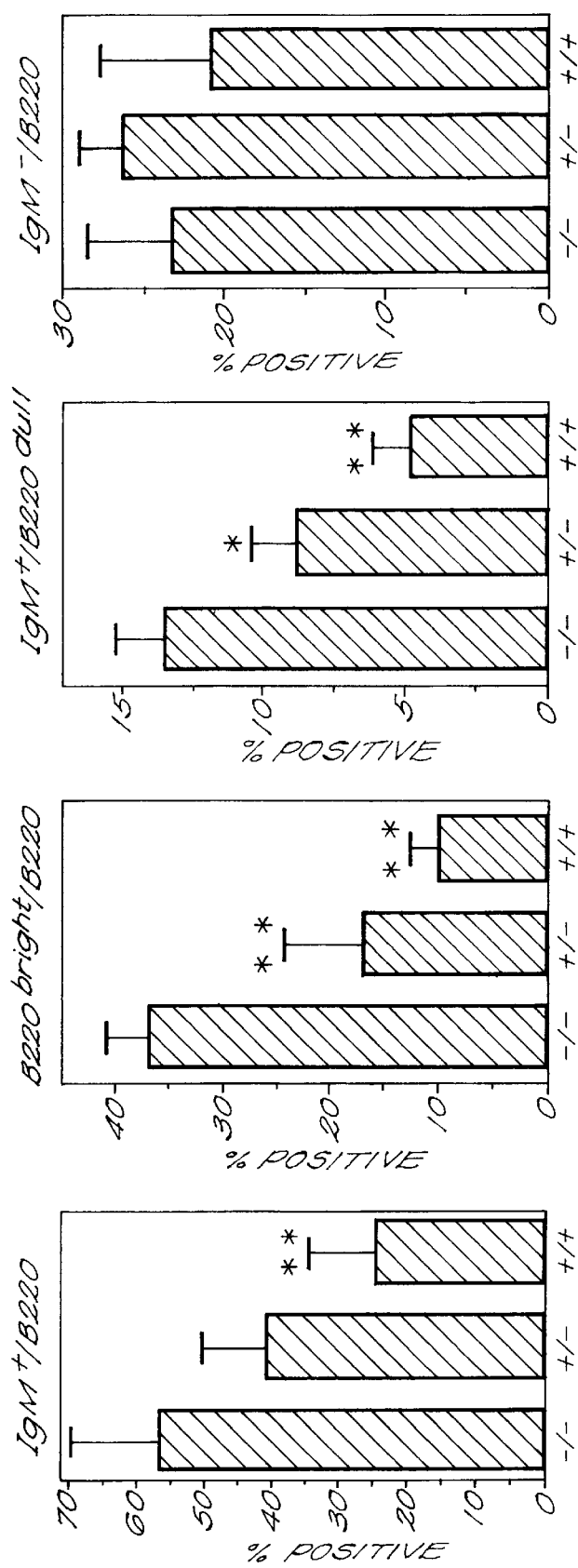

REGULATORY ELEMENTS CONTROLLING TISSUE-SPECIFIC GENE EXPRESSION

The invention was made with government support, therefore the U.S. government has certain rights in the invention.

FIELD OF THE INVENTION

The invention relates in general to genetic regulatory elements.

BACKGROUND OF THE INVENTION

B lymphocytes develop from multipotential stem cells and mature into antibody-secreting plasma cells after passing through multiple differentiation stages. Pre-B cells express cytoplasmic $\mu$ heavy chain protein before developing into immature B cells that express surface IgM. This highly regulated process occurs primarily in the bone marrow and is antigen independent. Immediately prior to leaving the bone marrow, B cells mature to acquire surface IgM and IgD and the ability to respond to antigen. B cells also express other surface molecules indicative of B cell development, proliferation and differentiation. CD19 is a lineage-specific 95,000 mw glycoprotein expressed by B cells from about the time of immunoglobulin (Ig) heavy chain rearrangement until plasma cell differentiation. CD19 is a member of a multimeric cell surface signal transduction complex which includes TAPA-1, CD21, (CR2, C3d/Epstein Barr Virus receptor), Leu-13 and other unidentified proteins.

SUMMARY OF THE INVENTION

The invention is based on the discovery of recombinant DNA which includes regulatory elements that control expression of the CD19 gene in a B-cell-lineage-specific manner, and thus which result in restriction of the 95,000 mw protein encoded by the CD19 gene to the surface of cells of the B-lineage.

B-lineage-specific regulatory elements of the invention have nucleotide sequences encompassed within recombinant DNA of A.T.C.C. Deposit No. 69531.

The invention also encompasses a method of identifying B-cell-lineage regulatory elements which includes providing an isolated DNA fragment containing the CD19 coding region and 5' and 3' flanking sequences, which controls expression of this coding region in a B-cell-lineage-restricted manner, and shortening the length of the DNA fragment so as to retain B-cell-lineage-restricted control of expression of the coding region. The method may further include obtaining a DNA fragment of a minimum length which specifies B-cell-lineage-restricted control of gene expression by repeating the shortening step until such control is lost, wherein the shortest length of DNA which retains such control is the minimum length specifying control.

The invention also encompasses regulatory elements of the invention operationally associated with a heterologous gene, such as a gene whose expression is to be limited to cells of B-lineage, e.g., a gene compensating for an immunodeficiency syndrome.

The invention also encompasses a B-cell line transfected with recombinant DNA including the regulatory elements described herein operationally associated with a coding region. As used herein, "operationally associated" refers to an association of the regulatory element(s) with a coding region which results in expression of the coding region as its encoded mRNA and/or protein.

B-cell-lineage regulatory elements of the human CD19 gene also operate within a transgenic environment, i.e., confer expression of the human CD19 gene in a B-lineage-restricted manner to B cells of non-human mammals. The invention thus also encompasses a transgenic mouse, i.e., a mouse having in its germline a gene encoding human CD19, which gene is regulatable in the mouse in a B-cell-lineage-restricted manner.

As used herein, "B-cell-lineage-restricted" expression refers to a pattern of expression which is restricted to B cells, pre-B cells and/or pro-B cells. B cells include cells of the immune system which are at a stage of maturation in which they are destined to undergo immunoglobulin heavy chain gene rearrangement or have undergone such rearrangement; such cells are limited to cells which contain in their cytoplasm or preferably on their cell surface the 95,000 mw CD19 glycoprotein. B cells also may include cells having other B-cell-specific surface markers, such as MHC II, CD20, and/or CD72. Thus, B-cell-lineage will include cells found in the B cell areas of lymph nodes and in the white pulp and red pulp of spleen, some lymphocytes in the small intestine, consistent with the rare presence of B cells in this tissue, scattered cells in the thymus medulla, again consistent with the rare presence of B cells, and also includes $B220^+$ cells, which occur in bone marrow and spleen. Conversely, B-lineage cells excludes cells or tissues such as $CD3^+$ or $Thy1.2^+$ T cells, monocytes, granulocytes or other hematopoietic cells, or cells of the stomach, liver, brain, uterus or kidney.

As used herein, "regulatory element(s)" is meant to include but is not limited to one or more of the following: a promoter which promotes transcription of a gene, an enhancer which increases the level of gene transcription, and a suppressor which suppresses transcription of a gene. Any or all of these elements may confer B-lineage-specificity, i.e., may operate to regulate expression of a gene in a tissue or cell-type-specific manner.

"Immunodeficiencies" relating to B-cells refers to deficits of molecules which reside on the surface of or within pro-B, pre-B or mature B cells, or which are produced by such cells. Examples of such deficiencies are described herein, e.g., X-linked gammaglobulin anemias and immunodeficiency diseases.

These and other embodiments of the claims will be apparent from the detailed description and the claims.

BRIEF DESCRIPTION OF THE DRAWINGS

The invention will be more fully understood from the following exemplary detailed description taken in conjunction with the accompanying drawings in which:

FIGS. 3A–3G are a schematic illustration of DNA constructs designed to determine the minimum elements necessary for B-cell-restricted gene expression.

FIG. 4A is an illustration of DNA fragments from human genomic DNA clones hB4G-7 and hB4G-10 which were linearly assembled to produce the hCD19 transgene.

FIG. 4B is an illustration of a genomic fragment of human DNA that includes all hCD19 exons, ~4.5 kb of 5' upstream DNA and ~4.7 kb of 3' DNA.

FIG. 10A-1–10A-4 are a series of histograms showing the expression of hCD19 by bone marrow cells from two month old h19-1 transgenic mice. The histograms in each of FIG. 10A-1–FIG. 10A-4 represent the result from control littermate, heterozygous and homozygous samples, respectively.

FIG. 10B-1–FIG. 10B-4 is a series of histograms showing the expression of hCD19 by bone marrow cells from two week old h19-1 transgenic mice. The histograms in each of FIG. 10B-1–10B-4 represent the results from control littermate, heterozygous and homozygous samples, respectively.

DESCRIPTION OF PREFERRED EMBODIMENTS

Figure 1:
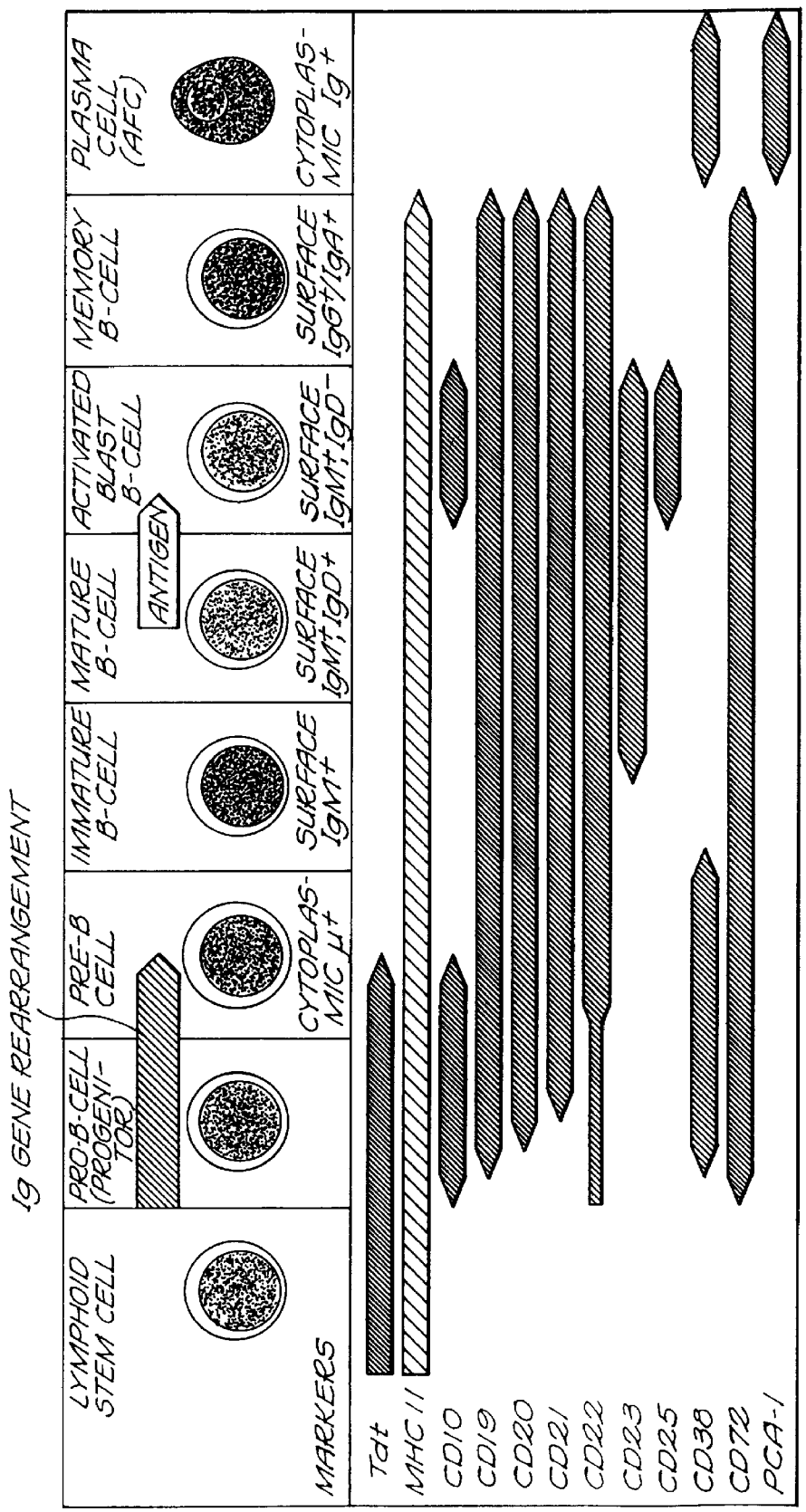
FIG. 1 is a chart of the prior art illustrating the B cell differentiation pathway, with associated cell surface markers.

The invention includes regulatory elements which restrict gene expression to cells of B-lineage. B-lineage cells include lymphoid stem cells whose maturation is committed to immunoglobulin producing cells, including pro-B (i.e., progenitor B) cells, pre-B cells, immature B cells, mature B cells, activated/blast B cells, memory B (IgM-producing) cells, and plasma (IgG-producing) cells. The B cell differentiation pathway is shown in FIG. 1.

B cells differentiate from lymphoid stem cells into virgin B cells and may then be driven by antigen to become memory cells or plasma cells. The genes coding for antibody are rearranged in the course of progenitor cell development. The characteristic markers of cells of B lineage are immunoglobulins, which act as cell-surface antigen receptors. Lymphoid stem cells (probably expressing terminal deoxynucleotidyl transferase, Tdt) proliferate and differentiate and then undergo immunoglobulin gene rearrangements. Following this, they emerge as pre-B cells which express $\mu$ heavy chains in the cytoplasm.

A sequence of immunoglobulin gene rearrangements and phenotypic changes takes place during B cell ontogeny. Heavy chain gene rearrangements occur in B cell progenitors and represent the earliest indication of B lineage commitment. This is followed by light chain gene rearrangements which occur at later pre-B cell stages. Certain B cell surface markers are expressed prior to immunoglobulin detection, namely class II MHC molecules, CD19, CD20, CD21 and CD10. The latter marker is a highly conserved neutral endopeptidase which is transiently expressed on early B progenitors before the appearance of heavy A chains in the cytoplasm. CD10 is re-expressed later in the B cell life history, following activation by antigen. CD38 is an example of a molecule found on early progenitors that is lost, only to reappear on the fully differentiated plasma cells. Tdt is also expressed very early in ontogeny. Other markers such as CD23 and CD25 (IL-2 receptor alpha) are mostly found on activated B cells. PCA-1 is found only on plasma cells.

Pre-B cells express cytoplasmic $\mu$ chains only. The immature B cell has surface IgM, and the mature B cell other immunoglobulin isotypes. On antigen stimulation the B cell proliferates and develops into a plasma cell or a memory cell following a phase of proliferation, activation and blast transformation. FIG. 1 also shows the sequence of appearance of other B cell surface markers.

A number of growth and differentiation factors are required to drive the B cells through early stages of development. Receptors for these factors are expressed at various stages of B cell differentiation. IL-7, IL-3 and low molecular weight B cell growth factor (L-BCGF) are important in initiating the process of B cell differentiation whereas other factors are active in the later stages.

Following their production in the fetal liver, B cells migrate and function in the secondary lymphoid tissue. sIgM$^+$ cells which carry a T cell marker (CD5) are early immigrants into fetal lymph nodes (17 weeks in humans). CD5$^+$ B cell precursors are found in the fetal omentum. Small numbers of CD5$^+$ B cells are also found in the mantle zone of secondary follicles in adult lymph nodes.

Following antigenic stimulation, mature B cells can develop into memory cells or antibody-forming cells (AFCs). Surface immunoglobulin (sIg) is usually lost by the plasma cell (the terminally differentiated form of an AFC), since its function as a receptor is finished. Immature and mature B cells respond in different ways to antigens. Treatment with anti-IgM antibodies or antigen results in loss of sIgM by capping and endocytosis in both mature and immature B cells. However, only mature B cells resynthesize sIgM in culture.

CD19 is a lineage-specific 95,000 M$^r$, glycoprotein expressed by B cells from about the time of immunoglobulin (Ig) heavy chain rearrangement until plasma cell differentiation. CD19-mediated signal transduction initiates a series of biological responses. Crosslinking of CD19 with monoclonal antibodies (mAb) induces an increase in the intracellular calcium ion concentration ($[Ca^{++}]_i$) of B cells and some B cell lines, and induces tyrosine kinase activity. CD19 and surface Ig are functionally linked, because mAb binding to CD19 inhibits the increase in $[Ca^{++}]_i$ that follows mitogen stimulation and subsequent B cell inactivation of normal calcium mobilization by crosslinked CD19. In addition, comodulation studies indicate that CD19 can cocap with cell surface Ig. CD19 mAb binding may also provide a proliferative signal for early IgM negative precursor B cells. Thus, CD19 may be involved in both positive and negative control of B cell proliferation depending on the stage of activation or differentiation.

CD19 has two extracellular Ig-like domains separated by a smaller potentially disulfide-linked domain, a membrane-spanning domain and an approximately 240 amino acid cytoplasmic domain that is highly charged. While a receptor function for the extracellular domain of CD19 has not been found, the transmembrane domain is required for the intermolecular association between CD19 and TAPA-1, and the evolutionarily conserved cytoplasmic domain is required for induction of increased $[Ca^{++}]_i$ mobilization in cooperation with surface Ig. The lyn protein tyrosine kinase is found to be associated with the CD19 cytoplasmic domain. The cytoplasmic domain of CD19 contains kinase insert regions that, when phosphorylated, mediate the binding and activation of phosphatidylinositol 3-kinase. CD19 may also serve an accessory role, functioning in conjunction with surface Ig to mediate antigen-driven B cell activation in response to low concentrations of antigen.

Figures 1, 10A:
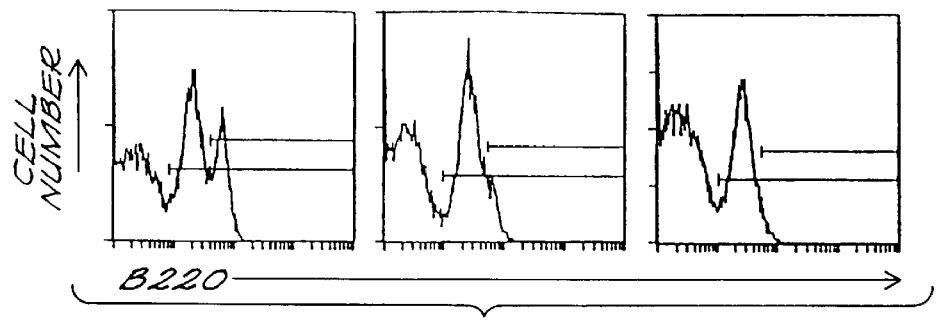
Figures 2, 10A:
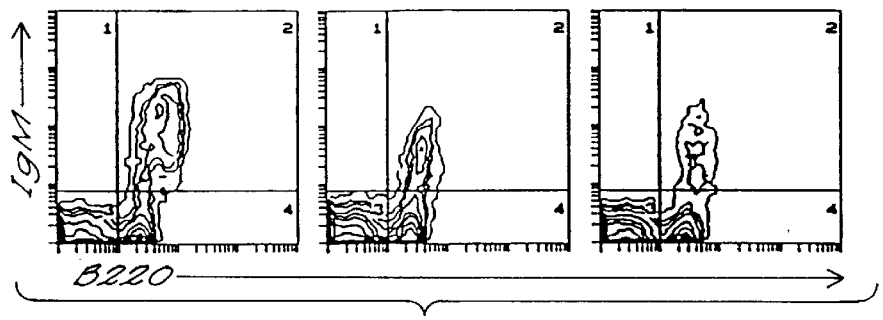
Figures 3, 10A:
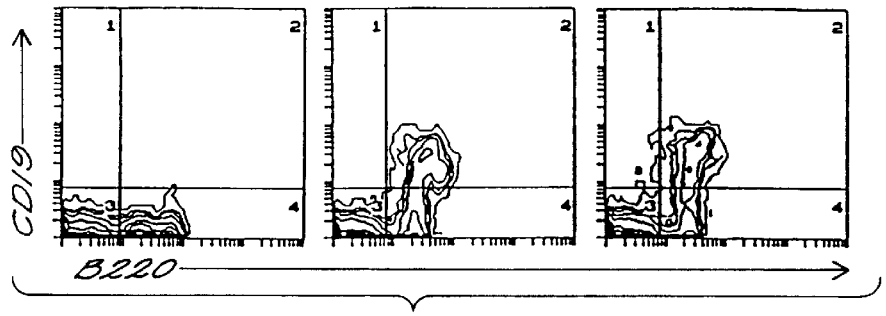

A genomic DNA fragment containing the human CD19 coding sequences, introns and flanking sequences is shown in FIGS. 3 and 4A and 4B. The restriction map of the region surrounding the human CD19 gene was constructed by single, double, or triple endonuclease digestions of lambda EMBL3 clones B4G-7, -10, -15, and -29 and their subclones. The locations of exons 1–15 is shown. Boxes represent exons sequences found in CD19 cDNAs, with the coding regions hatched, and the untranslated regions filled. TM indicates the transmembrane domain.

Cloning and sequencing of the human and mouse CD19 genes is described in Zhou et al., Immunogenetics 35: 102, 1992, hereby incorporated by reference. The structure and organization of the CD19 antigen of human, mouse, and guinea pig B lymphocytes is described in Zhou et al., Jour. Immunol. 147: 1424, 1991, hereby incorporated by reference.

A.T.C.C. DEPOSIT

A deposit of *Escherichia coli* containing human CD19 transgene in SP65 plasmid, B4G W/3UT in SP65, DH5a has been made at the ATCC, Rockville, Md. on Jan. 7, 1997 under the accession number 69531. The deposit shall be viably maintained, replacing it if it becomes non-viable, for a period of 30 years from the date of deposit, or for 5 years from the last date of request for a sample of the deposit, whichever is longer, and made available to the public without restriction in accordance with the provisions of the law. The Commissioner of Patents and Trademarks shall, upon request, have access to the deposit.

B-lineage regulatory elements of the invention are all contained within the 15 kb DNA fragment of A.T.C.C. Deposit No. 69531. This 15 kb fragment may be used to express the CD19 sequences or a contiguous heterologous coding sequence in a B-lineage-restricted manner. If a smaller fragment containing B-lineage specific regulatory elements is desired, such a smaller fragment may be constructed as follows.

In order to prepare a DNA fragment smaller than the above-described 15 kb fragment containing the minimal elements useful to generate B-lineage-restricted expression of the CD19 gene or a heterologous gene, the following procedures may be followed. These procedures will not simply identify the CD19 promoter and enhancer elements, but will produce the minimal portion of the CD19 gene which is necessary for lineage-restricted expression of CD19 or a heterologous gene.

FIG. 3 includes a restriction enzyme map of the 15 kb DNA fragment (construct A) which is known to confer B-lineage specific expression. contained within this 15 kb fragment are the B-lineage-restricted regulatory elements of the human CD19 gene. Using the 15 kb fragment, shorter transgenes may be constructed and tested for B-lineage restricted expression. The transgene constructs shown in FIG. 3 are meant to be constructed either independently of one another or in combination and tested for B-lineage-restricted expression of the CD19 or a heterologous coding region. First, CD19 exons may be removed as described by Palmiter et al., 1991, Proc. Nat. Aca. Sci. 88: 478–482. As shown in FIG. 3, the 5' end of the transgene may be truncated (construct B) by digesting the 15 kb fragment at any one of a number of restriction sites, several of which are shown in FIG. 3. As shown in FIG. 3, the 3' untranslated region may be removed (construct C) by digesting with XhoI. Also as shown in FIG. 3, the CD19 introns may be removed (construct D), again using restriction endonucleases, to provide the coding region shown in SEQ ID NO:1. Also as shown in FIG. 3, constructs may be made which combine the deletions (construct C) and (construct D). Construct F of FIG. 3 represents the minimal portion of the CD19 gene which is necessary for B-lineage specific expression of the gene. Construct G represents the minimal unit shown in construct F fused to a heterologous gene or cDNA in order to obtain B-lineage restricted expression of a heterologous gene. Of course, alternative heterologous gene fusions may be constructed and tested.

Testing for B-lineage-restricted expression may be carried out in mouse B and T cell lines by DNA transfections, as has been described herein for the 15 kb CD19 transgene (A.T.C.C. deposit no. 69531). The constructs may also be tested in the transgenic mouse system, as described herein, for B-lineage-restricted tissue-specific expression. Once the minimal elements for B-lineage-restricted gene expression are produced, these elements of the CD19 gene may be used to direct the expression of other transgenes in a B cell-restricted manner. Expression of the transgene may be amplified, if necessary, using other B-cell regulatory elements, such as the E mu-enhancer (Adams et al., 1985, Nature 318: 533–538; Alexander et al., 1987, Mol. Cell. Biol. 7: 1436–1444, both of which are hereby incorporated by reference). The above-described constructs also may be used in gene therapy, i.e., for directing the expression of genes whose products are necessary to replace B-cell gene products which are present at abnormally low levels or which are absent, also as described below.

The following examples are presented to illustrate the uses and advantages of the invention.

EXAMPLE I

In vitro testing of a fragment smaller than the above-described 15 kb fragment, which smaller fragment is suspected of conferring B-cell-specific regulation of CD19 expression, and thus B-cell-restricted gene expression, may be performed by substituting the smaller fragment for the 15 kb fragment in the in vitro system described below. In addition, testing of gene constructs including the smaller fragment linked to the CD19 coding region or the coding region from a heterologous gene may be tested in vitro for B-cell-restricted expression by substituting the heterologous construct for the 15 kb fragment in the in vitro system described below.

The hCD19 gene, as described above, is composed of 15 exons which span ~6.8 kb of DNA and short 5' and 3' flanking sequences that are conserved between human and mouse. To determine whether all of the regulatory elements necessary for lineage-restricted CD19 gene expression were proximal to the known exons, a genomic fragment of DNA that includes all CD19 exons, ~4.5 kb of 5' upstream DNA and ~4.7 kb of 3' DNA was used (FIGS. 4A and 4B). A selectable neomycin resistance marker (Stratagene, LaJolla, Calif.) was attached to the 3' end of the genomic DNA. As a positive control for CD19 expression without B-cell-restricted regulation. The human CD19 cDNA clone pB4-19, containing the 15 kb fragment, was cloned into the Bam Hl site of the retroviral vector pZipNeoSV(X), under the control of the SV40 promoter (ATCC No. 37149), so that the 5' end of the cDNA coincided with that of transcripts originating from the promoter in the long terminal repeat.

The pZipNeo5V(X)/pB4-19 construct and the hCD19(neo) transgene were used to individually transfect cell lines using the Cell-Porator Electroporation system (Bethesda Research Laboratories, Gaithersburg, Md.). Mouse and human cell lines used for in vitro transfection experiments were cultured in RPMl 1640 medium (Gibco, Grand Island, N.Y.) supplemented with 10% FCS (Hyclone Labs, Logan, Utah), 2 mM L-glutamine, 50 U/ml penicillin, and 50 $\mu$g/ml streptomycin. The parameters for electroporation were: 60 $\mu$g of DNA per $5\times10^6$ cells in 0.5 ml of DME medium (Gibco) on ice, 1.6 millifarads, 250 V/0.4 cm, using the high ohm setting. Transfected cells were selected for in medium with 1 mg/ml Geneticin (Gibco) added (0.5–1.0 mg/ml) for positive selection. Clones were isolated by limiting dilution of the cell population.

The following cell lines were transfected: the mCD19$^+$ lines 300.19 and 70Z (ATCC No. TIB158); the mCD19$^+$ B cell lines, AJ9 and A20 (ATCC No. TIB208); the CD19$^-$ mouse T cell line Yac (ATCC No. TIB150); the CD19$^-$ mouse myeloma cell line, Ag8.653 (ATCC No. CRL1580); the CD19$^-$ human T cell lines, Rex, HPB-All and Jurkat (ATCC No. TIB152); the CD19$^-$ myelomonocytic cell line, U937 (ATCC No. CRL1593); and the CD19$^-$ human erythroleukemia line, K562 (ATCC No. CCL243).

The protein encoded by the CD19 gene was detected using B4 antibody (Coulter Immunology Corp., Fla.). Of the cell lines transfected with the CD19 gene, only mouse pre-B cell lines (300.19 and 70Z), and mouse B cell lines (AJ9 and A20) expressed detectable levels of hCD19 on the cell surface, although cells from each line grew in medium containing G418 (FIG. 5). Thus, none of the transfected T-cell lines expressed detectable levels of hCD19. Southern blot analysis with the hCD19(neo) transfected 300.19 cells revealed an intact single-copy insert of the hCD19 transgene. The 300.19, Rex, Jurkat and K562 cell lines are capable of expressing hCD19 since transfection of these cells with the hCD19 cDNA with expression regulated by a SV40 promoter generated surface CD19 expression. Thus, the necessary promoter elements of the CD19 gene were present in the hCD19 transgene and this transgene was sufficient to mediate B cell-specific expression of hCD19 in murine B cell lines.

For testing of fragments smaller than the 15 kb CD19 transgene for B-cell-restricted gene expression, the truncated fragment may be linked to the neo marker, as described above and using conventional recombinant DNA techniques, and transfected into a B-cell line, e.g., A20, and a T-cell line, e.g., Yac. If the truncated fragment contains B-lineage-restricted regulatory elements, the CD19 protein should be detectable on the cell surface of transfected cells only of the B-cell-lineage. Alternatively, the CD19 mRNA may be detected in lieu of protein detection using Northern blotting analysis, as described herein.

EXAMPLE II

In vivo testing of B-lineage-restricted expression of a fragment suspected of conferring B-cell restricted regulation of CD19 expression may be performed by substituting the shortened CD19 fragment for the 15 kb fragment in the transgenic mouse system described below. In addition, gene constructs, in which the minimum B-cell-restricted regulatory elements are linked to a heterologous gene, may also be tested in vivo by substituting the heterologous construct for the 15 kb construct in the transgenic mouse system described below.

The ability to introduce and express cloned genes in transgenic mice permits a comprehensive analysis of the expression and function of multiple developmentally regulated genes and the phenotypic effects of altered gene expression. This approach also has advantages for examining the function of gene products since complex biological effects mediated by the transgene can be correlated with the quantity of gene product expressed. The transgenic mouse system allows analysis of complex signaling pathways for which satisfactory tissue culture models do not exist. As used herein, a "transgene" is a gene which is expressible or expressed across species lines, i.e., a gene from a first mammalian species which is expressible in a second mammalian species; preferably, the transgene is regulated in its transgenic environment in a manner which is similar if not identical to its regulation in its natural environment.

The transgenic mouse system was used to determine if regulated expression and specificity of the human CD19 (hCD19) gene occurs in mice, and to examine the role of CD19 in B cell development and function. The human CD19 gene was microinjected into fertilized mouse eggs, and transgenic mice with augmented CD19 expression were produced as follows.

1. Generation of the hCD19 Transgene and Production of Transgenic Mice.

The hCD19 gene is composed of 15 exons which span ~6.8 kb of DNA and ~200 bp 5' and 3' flanking sequences that are conserved between human and mouse (Zhou et al., 1992, Immunogenetics, 35, 102–111). To determine whether all of the regulatory elements necessary for lineage-specific CD19 gene expression were proximal to the known exons, a genomic fragment of human DNA that included all hCD19 exons, ~4.5 kb of 5' upstream DNA and ~4.7 kb of 3' DNA was used (FIGS. 4A and 4B). FIGS. 4A and 4B show the structure of the hCD19 transgene. In FIG. 4A, DNA fragments from human genomic DNA clones hB4G-7 (Hind III to Kpn l, and Kpn-1 to Xho l) and hB4G-10 (Xho1 to Hind III) were linearly assembled to produce the transgene. The Hind III site in hB4G-7 enclosed in parenthesis was located in the polylinker of the DNA clone. In FIG. 4B, the intron-exon organization of the transgene containing exons 1 through 15 with 4.5 kb of 5' flanking and 4.7 kb of 3' flanking sequence is shown. Exons are indicated by rectangles with speckled rectangles indicating translated sequence. The human CD19 (hCD19) transgene was constructed in the SP65 plasmid by the sequential insertion of fragments of genomic DNA containing the human CD19 gene and flanking sequences (FIGS. 4A and 4B). Two DNA fragments from the genomic clone hB4G-7 (Zhou et al., 1992, supra), from the 5' end of the clone to the unique internal Kpn-1 site and from the Kpn l site to the Xho l site were subcloned into a plasmid with the Xho 1/Hind III fragment of the 3' end of the gene from genomic clone hB4G-10. The total length of the transgene was ~16 kb with ~4.5 kb of 5' flanking sequence and ~4.7 kb or 3' flanking sequence. Unique Hind III restriction sites flanked the transgene allowing linearization and separation from the vector. Linearized transgene was first purified by electrophoresis on agarose gels followed by ion exchange column chromatography using Quiagen columns (Quiagen, Inc., Chatsworth, Calif.) or ELUTIP-D columns (Schleicher & Schuell, Keene, N.H.). The purified linear human CD19 gene DNA was microinjected into the male pronucleus of fertilized mouse eggs obtained from B6SJL female mice mated to males of the same cross. The eggs were reimplanted into pseudo-pregnant mice as described (Hogan et al., 1986, Manipulating the mouse embryo: A laboratory Manual, Cold Spring Harbor, hereby incorporated by reference), resulting in the birth of 37 pups. Transgenic founder mice were mated with C57BL/6J mice to propagate the transgenic lines. All progeny were identified as heterozygous or homozygous for the hCD19 gene by examining the gene copy number relative to the parental transgenic mice and human DNA. Eight mice carried the hCD19 gene and were called h19-1 through h19-8 (Table 1).

conjugated to PE and B220 mAb labeled with FITC. Fluorescence analysis was on a Coulter Elite flow cytometer. Founder mice were 14 months old, and had a subpopulation of $B220^+$ $CD19^-$ circulating cells that were not found in younger mice. The heterozygous and homozygous progeny were 2 months old at the time of analysis. Values for each

TABLE I

Characteristics of Blood Lymphocytes from hCD19 Transgenic Mice[a]

| | Founder Mice | | Heterozygous Mice | | | Homozygous Mice | | |
|---|---|---|---|---|---|---|---|---|
| Line # | Sex | Gene copy # | $CD19^+$ blood | $B220^+$ blood | $CD19^+$ blood | $B220^+$ blood | $CD19^+$ blood | $B220^+$ blood |
| controls | M + F | 0 | 0 | 60 ± 13 | 0 | 60 ± 12 | 0 | 60 ± 12 |
| h19-1 | M | 9–14 | 13 ± 3 | 26 ± 5** | 23 ± 2 | 23 ± 6*** | 7 ± 2 | 7 ± 2*** |
| h19-2 | F | ND | 11 ± 7 | 25 ± 9* | — | — | — | — |
| h19-3 | F | 1–2 | 12 ± 1 | 40 ± 4 | — | — | — | — |
| h19-4 | M | 2–3 | 12 ± 4 | 53 ± 15 | 46 ± 1 | 46 ± 1 | 30 ± 3 | 30 ± 3*** |
| h19-5 | F | 1–2 | 17 ± 14 | 30 ± 13* | 41 ± 2 | 41 ± 1* | 30 ± 2 | 30 ± 2** |
| h19-6 | F | ND | 7 ± 3 | 37 ± 15 | — | — | — | — |
| h19-7 | M | 1–2 | 3 ± 2 | 52 ± 2 | 45 ± 1 | 45 ± 1 | 49 ± 1 | 49 ± 1 |
| h19-8 | M | ND | 1 ± 1 | 61 ± 7 | — | — | — | — |

*The percentage of $B220^+$ cells in transgenic mice was significantly less than in control littermates, p < 0.05; p < 0.01; *p < 0.002.
All statistical comparisons were carried out using the one- or two-tailed Student's test.

All values in Table 1 represent the percentage of positive cells for a given surface antigen obtained from blood lymphocytes (based on side and forward light scatter) and represent results obtained on at least 3 different occasions for the founder mice and results from at least three heterozygous and homozygous mice. In all instances, the background percent of cells that were positive (<3%) were subtracted from the values presented. The frequency of fluorescence positive cells was determined by single-color analysis using a Coulter Profile flow cytometer.

Figure 6:
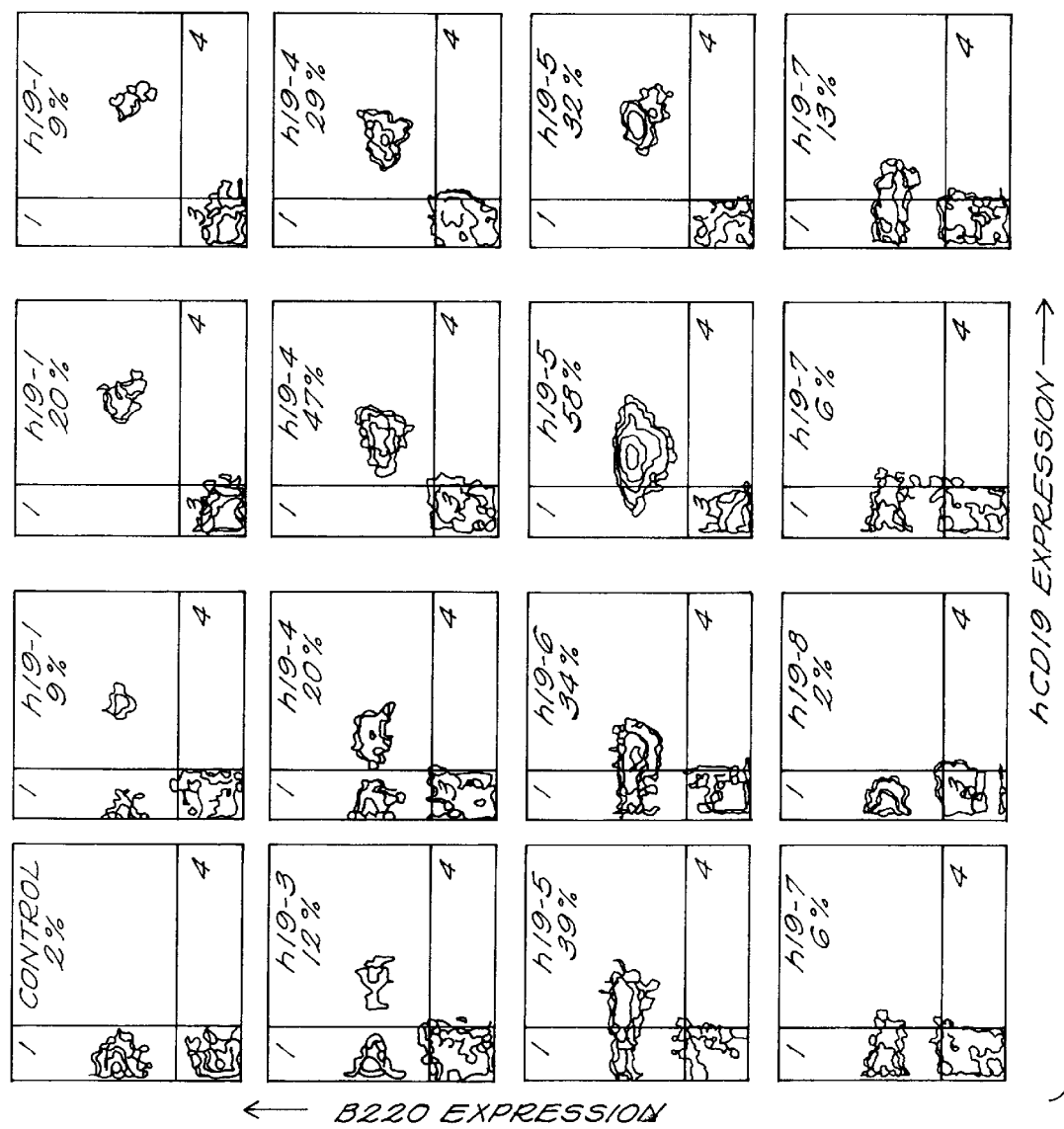
FIG. 6 is a series of histograms showing CD19 expression by blood leukocytes from control and transgenic mice.

Expression of the hCD19 gene product on the surface of peripheral blood leukocytes from the transgenic mice was examined by immunofluorescence staining using anti-human CD19 mAb and flow cytometry analysis. The following mAb were used in the flow cytometry analysis: phycoerythrin (PE)-conjugated B4 (anti-hCD19; Coulter, Hialeah, Fla.), M1/69 (anti-mouse heat stable antigen, Pharmingen, San Diego, Calif.); fluorescein isothiocyanate (FITC)-conjugated RA3-6B2 (anti-CD45R/B220) (Coffman and Weissman, 1981, Nature, 289, 681–685), B4 (anti-hCD19, Coulter), 145-2C11 (anti-mCD3) (Leo et al., 1987, Proc. Natl. Acad. Sci., USA, 84, 1374–1378), HO13.4 (anti-Thy1.2) (Marshak-Rothstein, et al., 1979, J. Immunol., 122, 2491–2497), Ig(5a)7.2 (anti-mouse IgDa allotype) (Oi and Herzenberg, 1979, Mol. Immunol., 16, 1005–1017); Ig(5b)6.3 (anti-mouse IgDb allotype) (Oi et al, 1978, Curr. Top. Microbiol. Immunol., 81, 115–129), S7 (anti-mCD43) (Coffman and Weissman, 1981, supra), 53-7.8 (anti-Ly-1, Pharmingen); and biotin-conjugated M1/70 (anti-Mac-1) (Sanchez-Madrid et al., 1983, J. Exp. Med., 158, 586–602), 6C3 (anti-BP-1, Pharmingen) and RA3-6B2. Polyclonal antisera, FITC-conjugated goat anti-mouse IgM (Southern Biotechnology Associates, Birmingham, Ala.) and biotinylated goat anti-mouse IgM (Vector, Burlingame, Calif.) were also used. The hCD19 antigen was expressed on the cell surface at high (hCD19-1) to low (hCD19-7) levels by a subpopulation of lymphocytes in 7 of the founder lines. In each case, all of the $hCD19^+$ cells were $B220^+$ (Table 1, FIG. 6). FIG. 6 shows CD19 expression by blood leukocytes from control and transgenic mice. All studies were carried out at the same time by two color analysis using CD19 mAb (B4) histogram represent the percentage of $CD19^+$ $B220^+$ cells in the total lymphocyte population gated on forward and side-angle light scatter. Horizontal and vertical lines which divide the figures into four quadrants delineate negative and positive populations of cells as determined using an unreactive control mAb. Fluorescence intensity is shown on a four decade log scale. These values differ from results obtained using single-color analysis (Table 1) due to the requirement for compensation during two color analysis which lowers the fluorescence intensity of hCD19 staining.

To determine transgene copy number, Southern blot analysis was performed on genomic DNA from the transgenic mice. Mouse genomic DNA was extracted from the distal 1–1.5 cm of tails from 3 week old mice as described (Hogan et al., 1986, supra). Southern blot analysis was as described (Southern, 1975, J. Mol. Biol., 98, 503–517; Tedder et al., 1989, J. Immunnol., 142, 2560–2568). Ten μg of restriction endonuclease-digested DNA was electrophoresed in horizontal 0.08% agarose gels and transferred to nitrocellulose (Wahl et al., 1979, Proc. Natl. Acad. Sci. USA., 76, 3683–3687). Human DNA was isolated from Epstein-Barr Virus transformed blood lymphocytes. hCD19 cDNA inserts were isolated from plasmids, twice purified by agarose gel electrophoresis, $^{32}$P-labeled by nick translation (Rigby et al., 1977, J. Mol. Biol., 113, 237–251), and hybridized with the filters as described (Southern, 1975, supra). Hybridization was performed at 42° C. in the presence of 50% (v/v) formamide and the filters were washed with 0.2×SSC with 0.1% (w/v) SDS at 65° C. DNA fragment size was determined by co-electrophoresis of a 1-kb ladder (Bethesda Research Laboratories, Gaithersberg, Md.). The hCD19 cDNA probe, pB4-17, was similar to the published pB4-19 cDNA (Tedder and Isaacs, 1989, J. Immunol., 143, 712–717) except it begins with the G of the translation initiation codon and terminates 22 nucleotides 3' of the poly(A) attachment signal sequence and has 17 3' A's attached. Three discontinuous mCD19 cDNA, mB4-211A1, mB4-30, mB4-503.1, that span from nucleotide position 98 to the poly (A) tail as shown (Zhou et al., 1991, J. Immunol., 147, 1424–1432) were used as probes for Southern analysis. Transgene copy number was determined by quantifying the level of hybridization of a hCD19 CDNA (AP17-1) probe with the same amount of genomic DNA from the human Namalwa B cell line, normal mice and transgenic mice blotted onto nitrocellulose. The cpm obtained for triplicate dot-blot determinations were compared with the cpm obtained with human DNA which contains two copies of the CD19 gene.

Southern blot analysis using genomic DNA from the transgenic mice and human genomic DNA revealed that transgene copy number varied from ~1 to ~14 in the different transgenic lines, with a positive correlation between gene dosage and the intensity of hCD19 expression on mouse B cells (Table 1, FIG. 6). Since only 40–80% of the B220$^+$ cells in the founder mice were hCD19$^+$ it is likely that the founder mice were chimeric for the hCD19 transgene. Four of the transgenic founder mice generated offspring carrying the transgene when mated with C57BL/6J mice. The frequency of germline transmission of the transgene was 67%, 10%, 67% and 25% for the h19-1, h19-4, h19-5 and h19-7 lines, respectively. In homozygous transgenic mice, cell surface hCD19 expression was approximately two fold higher than that of the heterozygous transgenic mice and all B220$^+$ cells expressed hCD19 (FIG. 6). Thus, the regulatory elements of the hCD19 gene necessary to mediate expression in murine B cells are present in the hCD19 transgene.

2. Expression of the hCD19 Transgene is Restricted to B-lineage Cells.

The pattern of hCD19 transgene expression was examined by Northern blot analysis of RNA isolated from spleen, thymus, heart, brain, lung, muscle, liver, thyroid and kidney of heterozygous transgenic mice (h19-1) and control littermates.

RNA was extracted from tissues dissociated with a homogenizer (Konet Glass Co., Vineland, N.J.) in the presence of 4M guanidine isothiocyanate as described (Sleasman et al., 1990, Eur. J. Immunol., 20, 1357–1366). Northern blot analysis was carried out using formaldehyde as a denaturing reagent. Ten $\mu$g of total cellular RNA was run in each lane and intact RNA was visualized in the agarose gel using ethidium bromide. pB4-17 was used as the probe, with hybridization at 42° C. in the presence of 50% formamide. The nitrocellulose filter was washed in 0.2×SSC at 65° C. after hybridization. mRNA size was determined by comparison with 28S and 18S ribosomal RNA.

Figure 7:
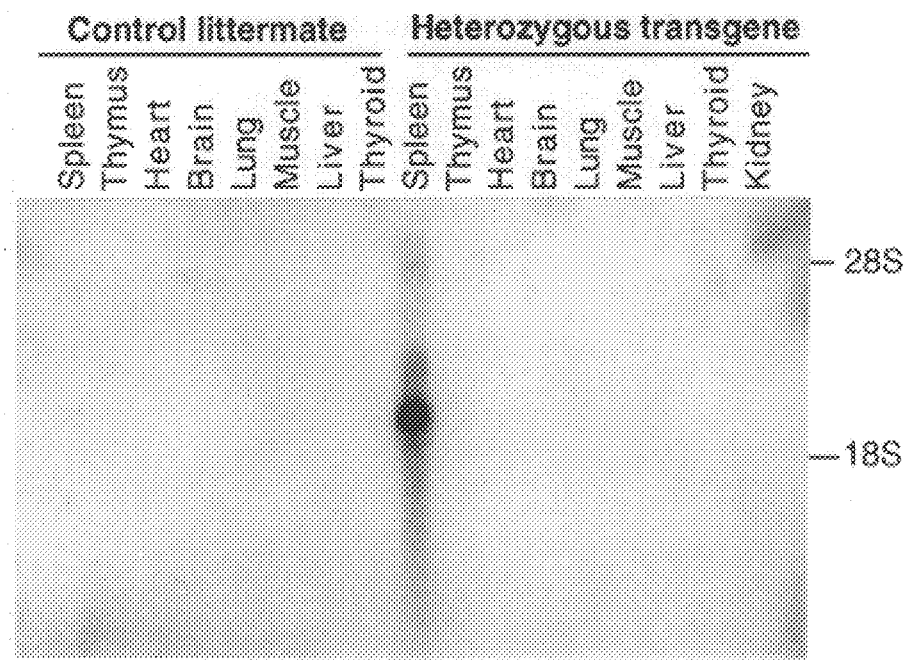
FIG. 7 is a Northern blot of RNA from tissues of a heterozygous h19-1 mouse and a control littermate probed with labeled pB4-17 human CD19 cDNA.
Figure 8A:
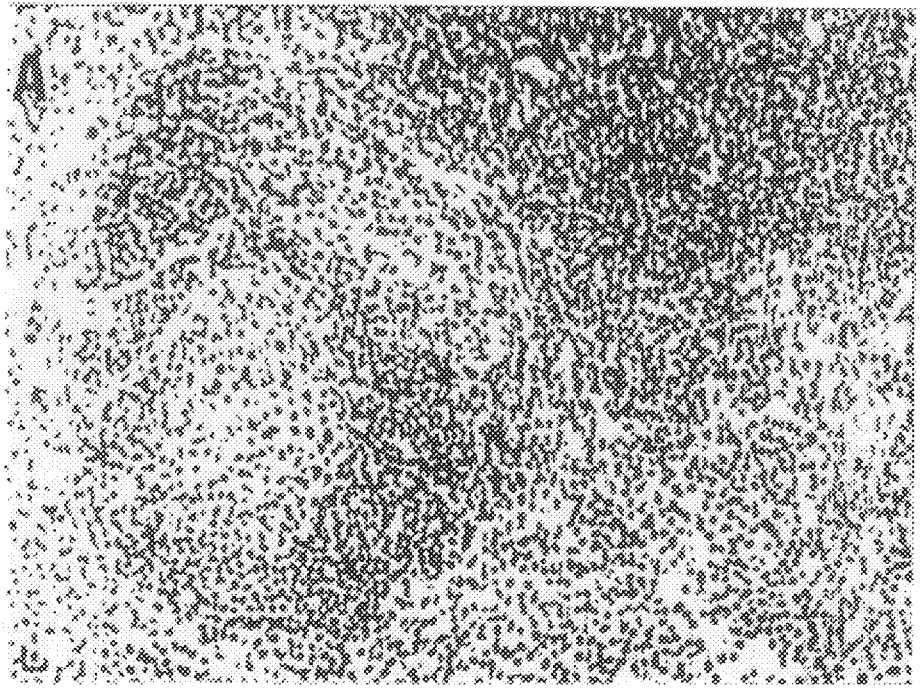
FIGS. 8A–8D are immunohistochemical analyses of hCD19 transgene expression in heterozygous transgenic hCD19 mice (B, D) and control littermates (A, C).
Figure 8B:
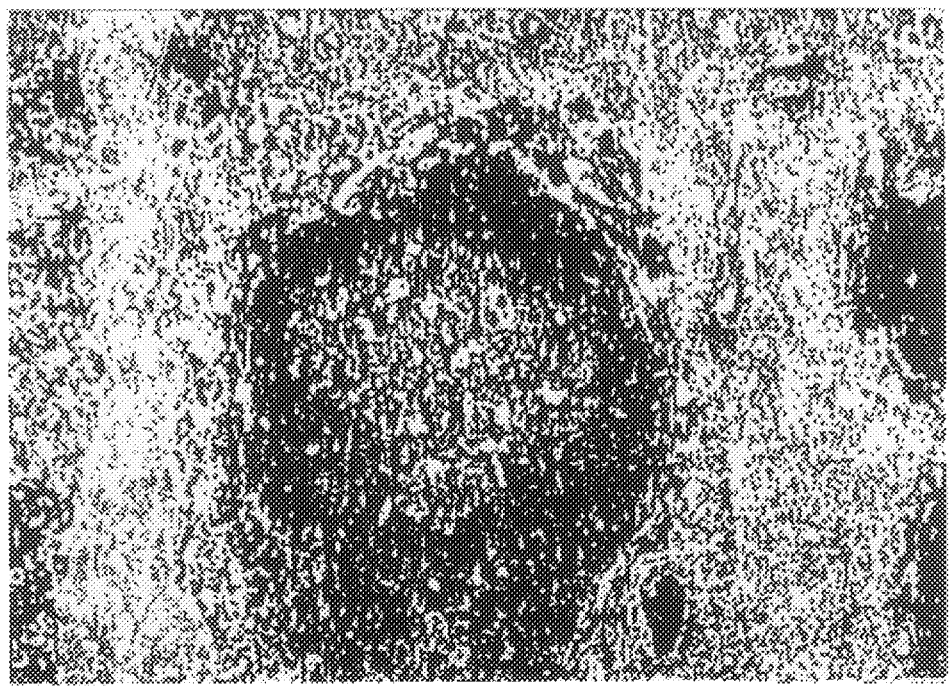
Figure 8C:
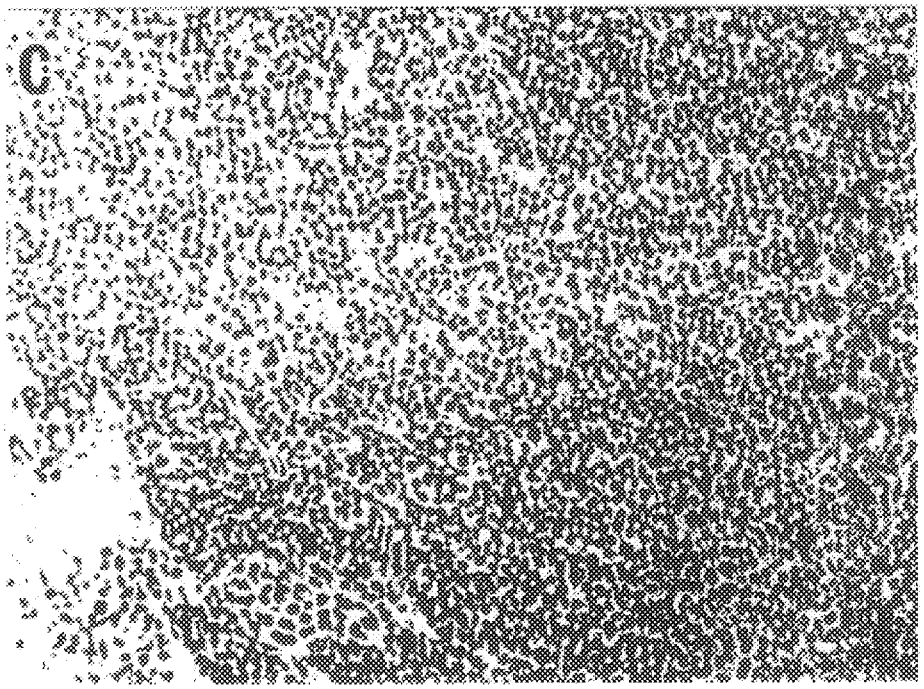
Figure 8D:
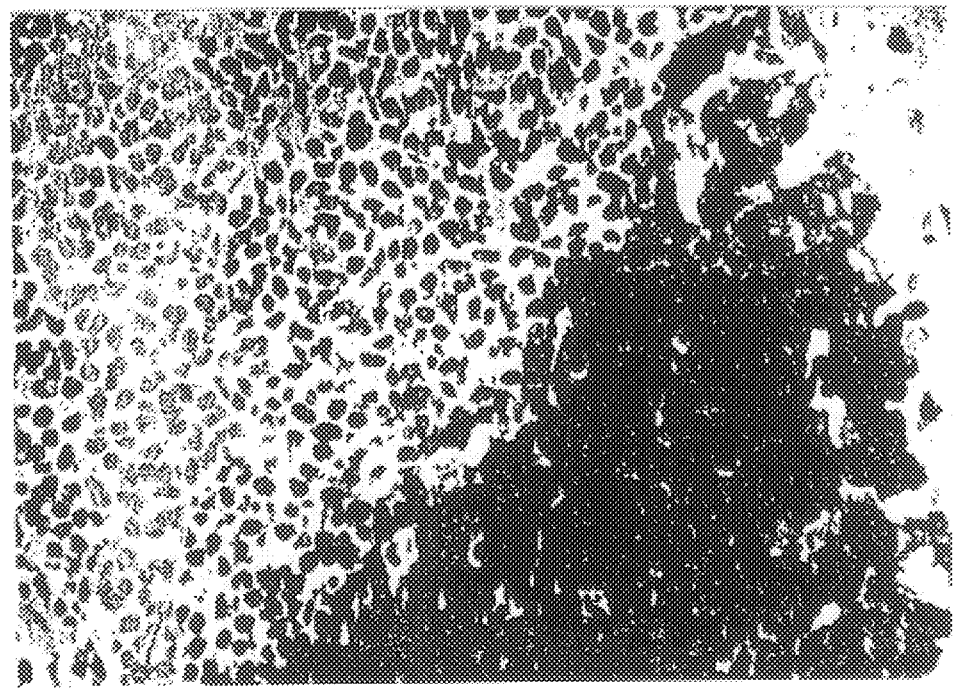

The hCD19 cDNA probe hybridized only to RNA isolated from the spleen of transgenic mice. No hybridization was detected with RNA from other tissues or control mice under high stringency conditions (FIG. 7). FIG. 7 shows that the CD19 transgene is expressed in the spleen of transgenic mice, but not in other tissues. Northern blot analysis of RNA from tissues of a heterozygous h19-1 mouse and a control littermate was probed with labeled pB4-17 human CD19 cDNA. Nitrocellulose filters were washed under high stringency conditions so that the hCD19 CDNA does not bind to mCD19 mRNA. Ribosomal RNA was run in parallel as an indicator of size, and to verify that the RNA was intact. Autoradiography was for 1 week with an intensifying screen. The predominant mRNA species was ~2.4 kb, with additional mRNA species of 2.8, 3.1 and 3.7 kb, as seen in human B cell lines (Tedder and Isaacs, 1989, supra). When the same Northern blot was probed with a mouse CD19 (mCD19) cDNA probe, only RNA from spleen hybridized and the level of hybridization was identical between transgenic mice and control littermates under high stringency conditions. Thus, expression of the hCD19 gene had no obvious effect on endogenous mCD19 gene expression, and hCD19 mRNA was expressed exclusively in lymphoid tissues.

Cells from bone marrow, spleen, thymus, peripheral blood and the peritoneal cavity of transgenic mice were further examined for hCD19 expression by immunofluorescent staining with flow cytometry analysis. Single cell suspension of mouse peripheral blood leukocytes, splenocytes, thymocytes, bone marrow cells and peritoneal cavity cells were isolated and examined immediately by immunofluorescence analysis. One color direct immunofluorescence analysis was performed as described (Coffman and Weissman, 1981, supra) by using FITC-conjugated B220 (RA3-6B2), and anti-B4 mAb. Two-color immunofluorescence staining was performed using FITC-conjugated antibodies in combination with biotinylated antibodies. Streptavidin-PE (Fisher Scientific, Fair Lawn, N.J.) was used to reveal biotin-coupled antibody staining. Cells were washed and analyzed on an Epics Profile flow cytometer (Coulter Corporation, Hialeah, Fla.). Ten thousand cells were analyzed for each sample. Normal tissues were obtained from transgenic mice and their littermates and kept in liquid nitrogen until use. Frozen tissue sections were air dried overnight, and subsequently fixed in acetone for 10 min. The sections were incubated with a biotinylated primary anti-CD19 mAb (HB12) for 30 min., washed with Tris-buffered saline (pH 7.8), and processed as described (Cordell et al., 1984, J. Histochem. Cytochem., 31, 219–229).

Among mouse peripheral blood leukocytes, only B220$^+$ cells expressed the hCD19 transgene (FIG. 6). Similar analysis of thymocytes, splenocytes and bone marrow cells revealed that only B220$^+$ cells were hCD19$^+$ in each tissue. In all cell populations examined, CD3$^+$ or Thy1.2$^+$ T cells, monocytes, granulocytes or other hematopoietic cells failed to express detectable levels of hCD19. Similar results were obtained for the founder mice, heterozygous and homozygous offspring, indicating that hCD19 transgene expression was restricted to the B lineage among hematopoietic cells.

Figures 4, 10A:
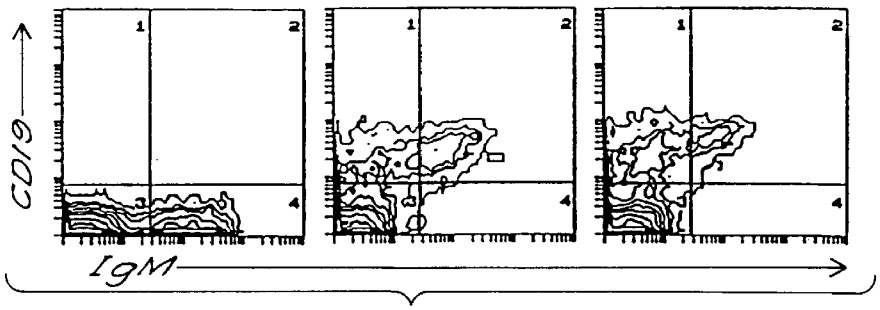

Immunohistochemical staining was performed on mouse spleen, lymph nodes, thymus, brain, heart, kidney, liver, lung, stomach, small intestine, uterus and skin tissue sections. The pattern of hCD19 expression in the transgenic mice was identical to that found in normal human tissues (FIG. 8). Expression of hCD19 was not detected in any of the indicated organs from normal mice, nor was it found in stomach, liver, brain, uterus or kidney of heterozygous h19-1 transgenic mice. hCD19$^+$ cells were found in the B cell areas of lymph nodes, and in the white pulp and red pulp of spleen in both heterozygous and homozygous animals. Some hCD19$^+$ lymphocytes were found in the small intestine, consistent with the rare presence of B cells in this tissue. Similarly, scattered hCD19$^+$ cells were found in the thymus medulla of heterozygous hCD19-1 mice, again consistent with the rare presence of B cells. FIG. 4 shows immunohistochemical analysis of hCD19 transgene expression in heterozygous transgenic hCD19-1 mice (B,D) and control littermates (A,C). Follicular B cell areas in spleen (A, B; X200) and lymph node (C, X200; D, X400) were hCD19$^+$ in transgenic mice, while no cells in control mice were hCD19$^+$ as determined by the APAAP staining technique. hCD19 transgene expression was therefor restricted to cells of the B lineage in all tissues examined.

3. Expression of the hCD19 Transgene Alters the Frequency of Mature B Cells.

Figure 9A:
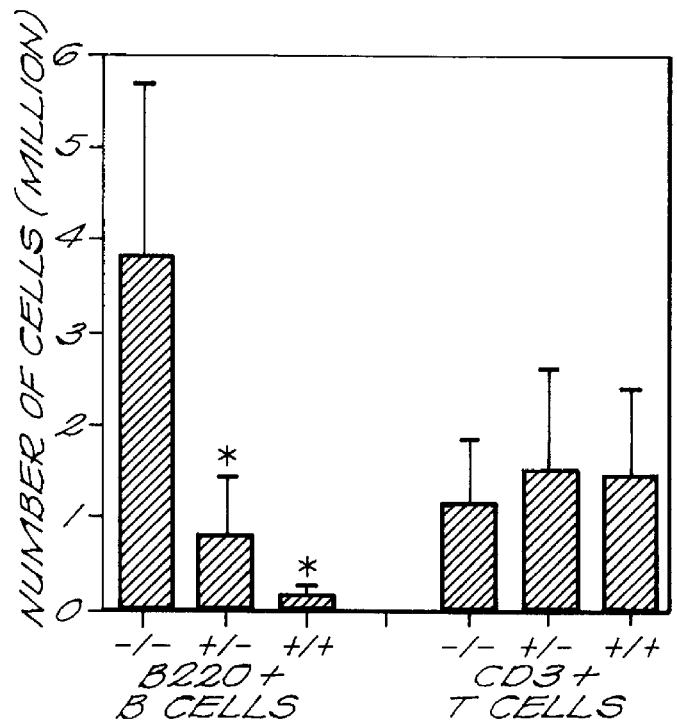
FIG. 9A and FIG. 9B show graphs of how hCD19 expression in transgenic mice alters the frequency of B lymphocytes in blood and spleen, respectively.
Figure 9B:
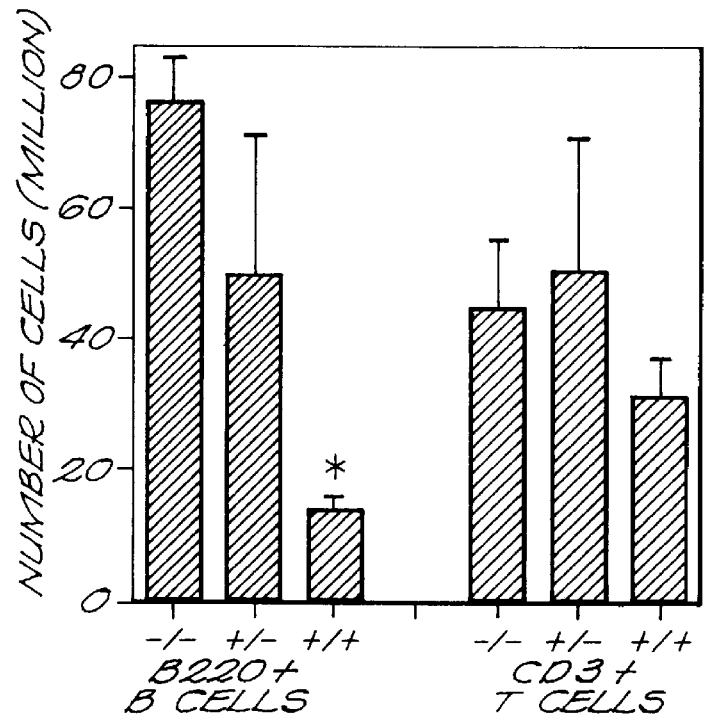

The expression of the hCD19 transgene correlated inversely with the number of circulating B220+cells: i.e., high levels of hCD19 expression resulted in decreased numbers of circulating B cells (FIG. 6, Table 1). Although evident in the founder animals, this effect was particularly apparent in homozygous and heterozygous transgenic mice in comparison to control littermates (Table 1). For example, heterozygous h19-1 mice had only 22% of control numbers of circulating B cells (p<0.001) while homozygous mice had only 4% of normal numbers (p<0.001) (FIG. 9). FIG. 9 shows that CD19 expression in transgenic mice alters the frequency of B lymphocytes in blood and spleen. The numbers of lymphocytes were based on the determined number of blood leukocytes per unit volume and the total number of mononuclear cells isolated from the whole spleen of 2 to 3 month old mice. The percentage of B220$^+$ B cells and CD3$^+$ T cells was then determined by flow cytometry. Results represent mean values (±SD) obtained for blood isolated from 12 control littermates, 10 heterozygous and 9 homozygous mice and with spleen cells isolated from 6 control littermates, 6 heterozygous and 4 homozygous mice.

Similar results were obtained for the number of spleen B220$^+$ cells, where spleen weight in 2 to 3-month-old homozygous transgenic mice was reduced by 30–40% compared to that of the control littermates. Determination of the number of nucleated cells per spleen revealed that heterozygous h19-1 transgenic mice had only 65% as many B cells (p=0.016), while homozygous mice had only 18% of the normal number (p<0.001) (FIG. 9). In contrast, the number of circulating and spleen T cells in the transgenic mice were not significantly different from control mice (FIG. 9). Similar results were obtained with other transgenic mouse lines with the decrease in B cell numbers correlating directly with increased levels of hCD19 expression (Table 1, FIG. 6).

The peritoneal cavity is populated in part by a distinct subset of B cells characterized by the expression of the CD5 (Ly-1) surface antigen (Kantor, 1991, Immunol. Today, 12, 389–391). All of the B220$^+$ cells in the peritoneal cavity of homozygous transgenic mice expressed hCD19, including the subpopulation of cells that expressed low levels of B220 and Mac-1 (CD11b), and high levels of surface IgM, a phenotype characteristic of CD5$^+$ lineage of B cells. While the percentage of conventional B cells in the peritoneal cavity of 2 month old transgenic mice was decreased, the percentage of CD5$^+$ B cells present was similar to that of control littermates.

One explanation for the decrease in peripheral B cell numbers in the hCD19 transgenic mice could be that these mice produce antibodies reactive with the hCD19, leading to removal of the B cells through normal immune-effector mechanisms. Therefore, serum (diluted 1:50) from 5 homozygous h19-1 mice and normal control littermates was examined for the presence of antibodies able to bind to the 300.19 mouse pre-B cell line expressing hCD19 by indirect immunofluorescence staining. In no case was antibody specific for hCD19 detected.

4. B Cell Development is Impaired in hCD19 Transgenic Mice.

Figures 1, 10B:
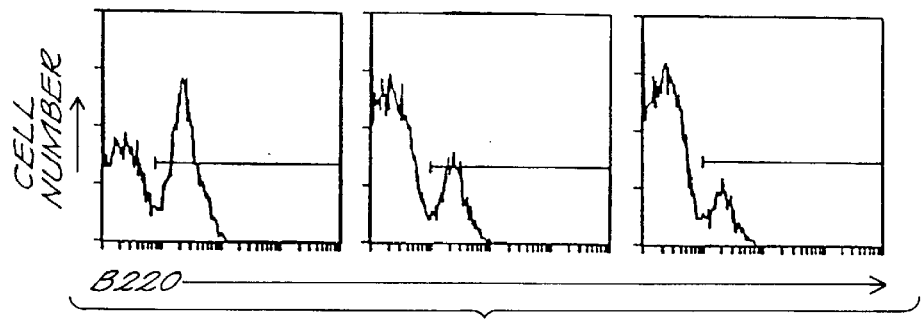
Figures 2, 10B:
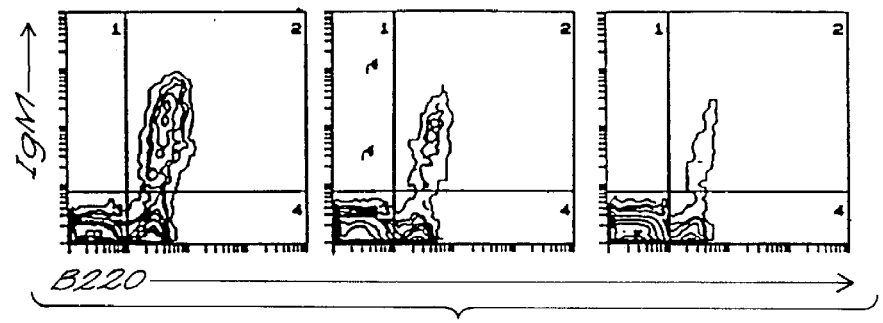
Figures 3, 10B:
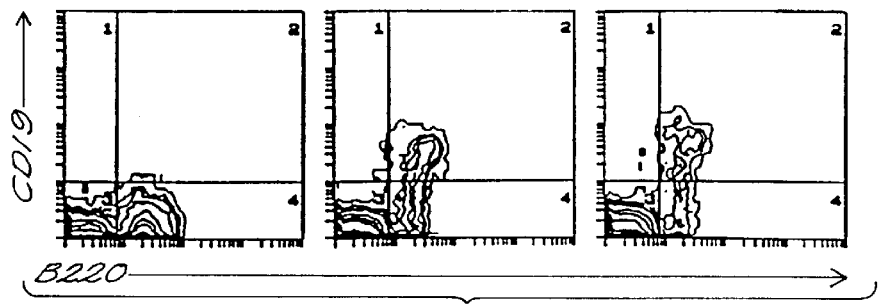
Figures 4, 10B:
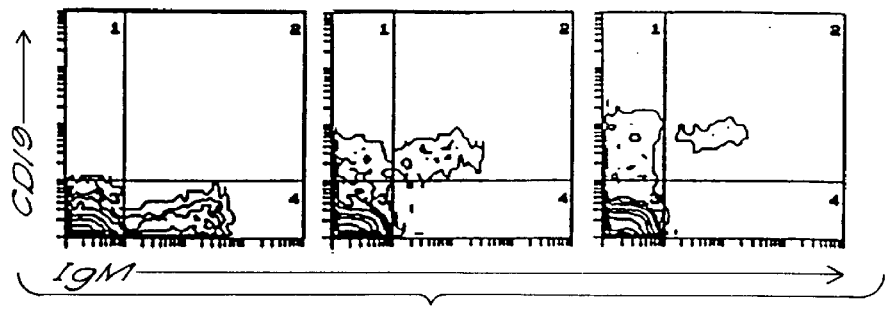

To determine when hCD19 is expressed during B cell ontogeny and to determine whether expression of the hCD19 transgene inhibits early B cell development, B-lineage cell populations present in bone marrow of h19-1 mice were analyzed. As in other lymphoid tissues, all hCD19$^+$ cells were B220$^+$ and all surface IgM$^+$ cells were hCD19$^+$ (FIG. 10). FIG. 10 shows that expression of hCD19 by bone marrow cells from h19-1 transgenic mice inhibits the development of immature B cells. In FIG. 10A, results are representative of those obtained from 2 month old control littermates (−/−; n=7), heterozygous (+/−; n=4) or homozygous (+/+; n=6) mice. In FIG. 10B, results are representative of those obtained from 2 week old control littermates (−/−; n=2), heterozygous (+/−; n=2) or homozygous (+/+; n=2) mice. Data is presented as in FIG. 7.

Figures 11A, 11B, 11C, 11D:
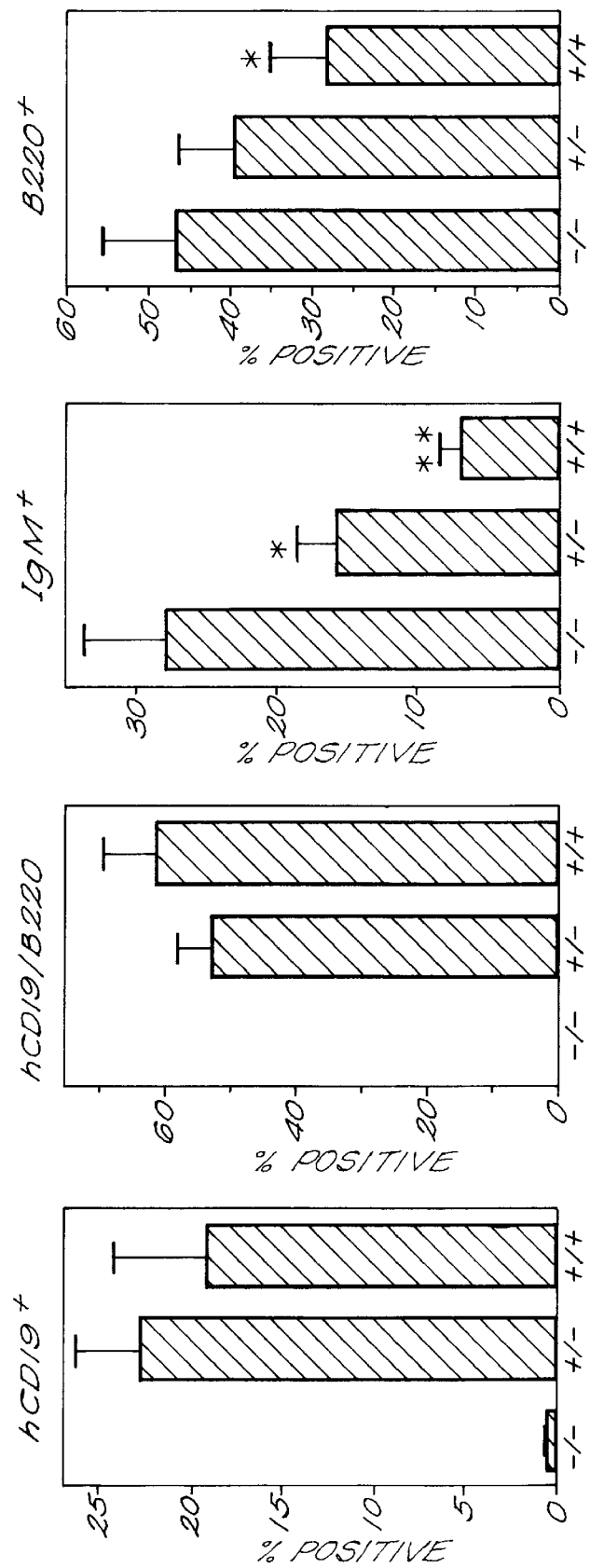
FIG. 11 contains graphs showing CD19 expression in lymphocyte populations present in bone marrow of hCD19 transgenic mice.

A substantial proportion of hCD19$^+$ cells were pre-B cells since only 50% of hCD19$^−$ cells expressed surface IgM (FIG. 10). Furthermore, ~20% of hCD19$^+$ cells expressed the S7 marker for early pro-B cells and 10% of the hCD19$^+$ cells expressed the BP-1 marker present on pre-B cells. Therefore, hCD19 was expressed during early pre-B cell development, as occurs in humans. B cell development in 2 to 3 month old heterozygous or homozygous h19-1 transgenic mice was significantly impaired as compared to control littermates. Most noticeable was that the B220$^{bright}$ IgM$^+$ (FIG. 10A) or IgM$^+$ IgD$^+$ (data not shown) mature B cell population in bone marrow was either significantly reduced or absent (p<0.001) FIG. 11. (FIG. 11 shows lymphocyte populations present in bone marrow of hCD19 transgenic mice.) These data are a summary (mean±SD) of results similar to those shown in FIG. 10 with 2 month old h19-1 mice; control littermates (−/−; n=7), heterozygous (+/−; n=4) or homozygous mice (+/+; n=6). Values represent the percentages of lymphocytes expressing the indicated cell surface markers was determined by two color immunofluorescence staining with flow cytometry analysis. For example, hCD19/B220 represents the percentage of B220$^+$ cells that are hCD19$^+$. *Indicates a significant difference relative to control littermates (p≦0.007, **indicates p≦0.001.

On average, the frequency of B220$^{bright}$ IgM$^+$ cells was reduced by 54% in heterozygous mice and was reduced by 73% in homozygous animals, compared to control littermates. The h19-1 transgenic mice also had significantly fewer B220$^{dull}$ IgM$^+$ newly generated B cells in the bone marrow, with a 35% reduction (p<0.007) in heterozygous mice and 64% reduction in homozygous mice (p<0.001). However, the percentage of IgM$^−$ B220$^+$ cells was unchanged in 2 month old mice, suggesting no apparent accumulation of pre-B cells in the bone marrow despite the decrease in the frequency of B cells (FIG. 11). Consistent with this, the frequency of CD43$^+$ (S7$^+$)B220$^+$ cells was similar in control mice (~5%, n=2) and homozygous littermates (~7%, n=2). Also, the frequency of BP-1/6C3 positive cells was ~6% (n=2) in heterozygous transgenic mice, and ~5% (n=2) in control littermates.

Similar results were obtained with 2-week-old heterozygous and homozygous h19-1 transgenic mice (FIG. 10B), except the proportion of IgM$^+$ B lineage cells in the bone marrow was more sharply reduced; 66% in heterozygous mice and 88% in homozygous mice. The frequency of B220$^+$ cells was also lower; 52% in heterozygous mice, and 69% in homozygous mice. However, the frequency of IgM$^−$B220$^+$ cells was not dramatically reduced between control littermates (20%, n=2), and heterozygous (16%, n=2) or homozygous (14%, n=2) mice. Consistent with the low frequency of immature B cells in the bone marrow, the frequency of B cells in the spleen of 2 week old transgenic mice was also significantly decreased. In the 10-1 line, control littermates had 23×10$^6$ (±3×10$^6$, n=2) splenic B cells, compared with 17×10$^6$ (±5×10$^6$, n=2) for heterozygous mice and 2×10$^6$ (±1×10$^6$, n=2) for homozygous mice. These results indicate that he bone marrow of transgenic mice produced normal numbers of IgM$^+$ pre-B cells and that the apparent block in B cell development induced by hCD19 expression occurred during the later stages of pre-B cell development at or about the time of surface IgM expression.

The frequency of bone marrow pre-B cells and B cells in cell cycle was examined in two month old homozygous and control littermates to determine whether the defect in B cell development resulted from an arrest of cell proliferation.

Single cell suspensions of bone marrow cells were stained with B220-FITC and biotinylated anti-IgM antibody. Streptavidin-PE was used to visualize IgM staining. After fixing with 4% formaldehyde (Fisher Scientific) the cells were incubated with the DNA dye DAPI (5 μm; 4',6-diamidino-2-phenylindole; Molecular Probes, Eugene, OR) in 0.4M Na phosphate buffer for 5 min on ice followed by analysis on an EPICS ELITE flow cytometer (Coulter Corporation) as described (Otto, 1990, Meth. Cell Biol., 33, 105–110). The DNA content of B220$^{dull}$ IgM$^-$ (pro- and pre-B cells) and B220$^+$ IgM$^+$ (immature and mature B cells) was quantified followed by mathematical analysis of the variability of DNA content.

In two experiments, the frequency of IgM$^-$B220$^+$ pre-B cells in $G_1$, S and $G_2$/M was 80–85%, 15–20% and <1%, respectively, in control mice. Pre-B cells from homozygous transgenic mice gave similar results with 75–86%, 14–25% and <1% being in $G_1$, S and $G_2$/M, respectively. In the IgM$^+$B220$^+$ B cell compartment, the frequency of cells in $G_1$, S and $G_2$/M was 96–98%, 0–1.4% and 0.5–4.2%, respectively, in control mice. B cells from homozygous transgenic mice gave similar results with 95–99%, 0–5.3% and 0–0.4% being in $G_1$, S and $G_2$/M, respectively. Therefore, it does not appear that cell cycle progression is appreciably affected by the expression of hCD19.

5. Signal Transduction through hCD19.

Stimulation of human B cells with CD19 mAb alone or in combination with suboptimal concentrations of anti-human Ig antibodies was determined as a measure of the change in $[Ca^{++}]_i$.

$[Ca^{++}]$ was measured as follows. Mouse spleen cells were isolated as a single cell suspension, treated with anti-CD3 and anti-Thy-1.2 mAb, and incubated with baby rabbit serum (Pel-Freeze, Brown Deer, Wis.) to lyse T cells. Spleen B cells (10 to 30×10$^6$) in 1 to 2 ml of RPMl 1640 medium were loaded with 1 μM indo-1-AM ester (Molecular Probes, Eugene, OR) at 37° C. for 30 min., washed and then resuspended at 0.5×10$^6$ cells/ml in RPMl. For analysis, the ratio of fluorescence (525/405 nm) of cells (5×105 cells/ml in 1 ml samples) was determined using an EPICS Elite flow cytometer. Baseline fluorescence ratios were collected for 30 seconds before specific mAb were added. CD19 mAb (unconjugated HB12b, i.e., anti-CD19, see Bradbury et al., 1992, J. Immunol., 149, 2841–2850) was added at a 1/200 final dilution of ascites fluid and goat anti-mouse IgM antiserum (Southern Biotechnology Associates, Birmingham, Ala.) was added at a 1/500 final dilution of the antiserum supplied by the manufacturer. A decrease in the fluorescence ratio indicates an increase in $[Ca^{++}]_i$.

Figure 12A:
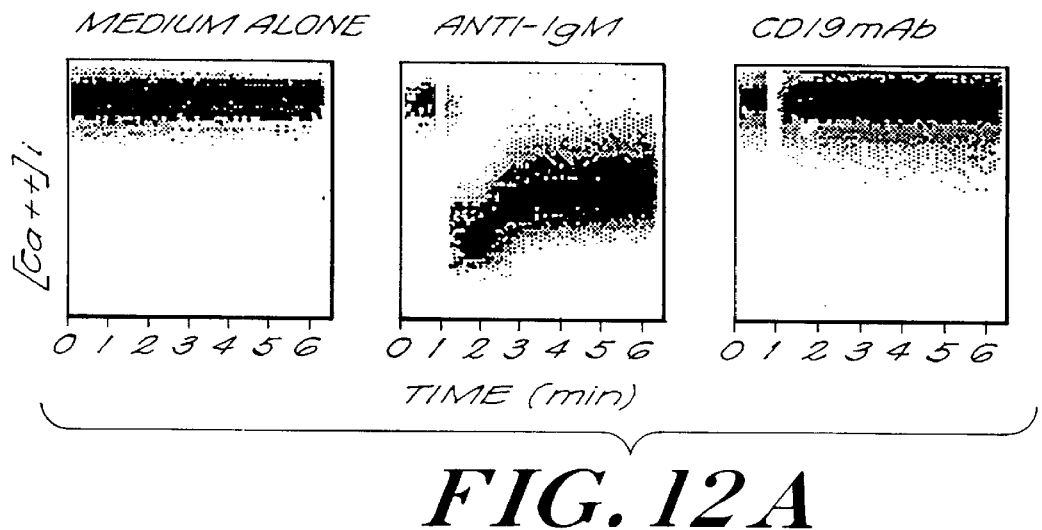
FIG. 12 is a series of histograms showing signal transduction through hCD19 in homozygous h19-1 spleen B cells.
Figure 12B:
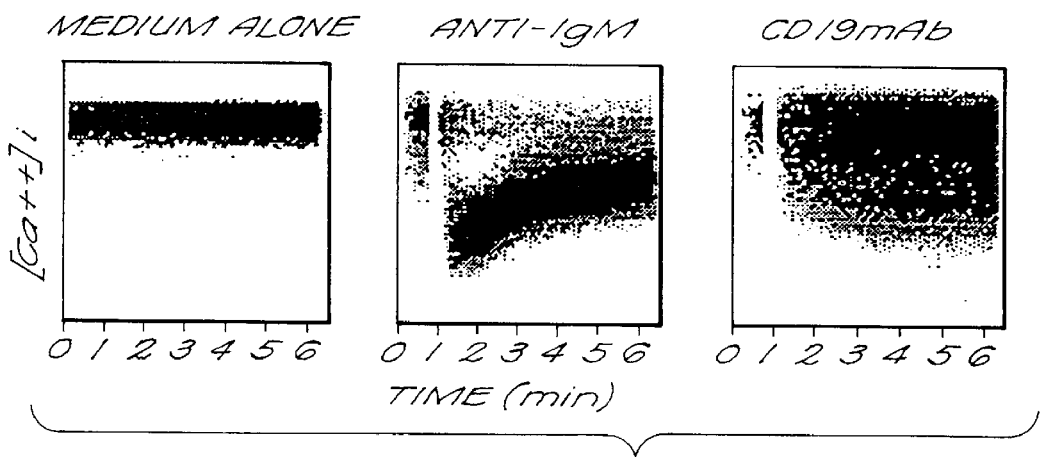

Stimulation of human B cells with CD19 mAb alone or in combination with suboptimal concentrations of anti-human Ig antibodies leads to an increase in $[Ca^{++}]_i$. Similarly, spleen B cells isolated from h19-1 homozygous transgenic mice increased $[Ca^{++}]_i$ in response to binding of anti-human CD19 mAb alone (FIG. 12). Spleen cells from control and transgenic mice increased $[Ca^{++}]_i$ in response to optimal doses of anti-mouse Ig antibodies to equivalent levels, demonstrating that the calcium signaling pathway in the transgenic mice was functional (FIG. 12). FIG. 12 shows signal transduction through hCD19 in homozygous h19-1 spleen B cells. B cells were isolated from the spleens of homozygous h19-1 mice or control littermates. These cells were then loaded with indo-1 and treated with anti-hCD19 (HB-12b) mAb, an optimal amount of anti-mouse IgM antibody or medium alone. An increase in $[Ca^{++}]_i$ over time is shown as a decrease in the ratio of indo-1 fluorescence. The gap in the histogram represents the time point at which the mAb was added. As observed with human B cells, the addition of anti-hCD19 mAb in combination with a suboptimal concentration of anti-mouse Ig antibody also resulted in an increase in the percentage of transgenic spleen cells which had an increase in $[Ca^{++}]_i$ (data not shown). In contrast, the addition of anti-human CD19 mAb alone did not alter the $[Ca^{++}]_i$ of spleen cells from control littermates and did not augment the response to suboptimal amounts of anti-mouse Ig antibodies. Taken together, these data suggest that the human CD19 molecule expressed in mouse cells may be functionally active and capable of signal transduction.

The ability of B cells to respond to antigen and mature into Ig-producing plasma cells in 2 to 3 month old transgenic mice was compared with that of control littermates. Sera from four homozygous transgenic mice was compared with that of four control littermates for Ig content.

Ig levels in sera were determined using an ELISA. Briefly, ELISA plates (Costar, Cambridge, Mass.) were coated with 100 μl (10 μg/ml) of goat anti-mouse IgG$_1$, IgG$_{2a}$, IgM, and IgA antibodies (Southern Biotechnology Associates) at 4° C. overnight, respectively. After washing 3 times with PBS containing 0.1% BSA, the plates were blocked by PBS with 1% fetal calf serum and 0.02% sodium azide for 1 hour at 37° C. The plates were washed 3 times and diluted mouse serum was incubated at 37° C. for 2 hours. Affinity purified mouse Ig of all isotypes (Southern Biotechnology Associates) were used as standards in the assay. Plates were washed 4 times with PBS/0.1% BSA and further incubated with alkaline phosphatase-conjugated isotype specific goat anti-mouse Ig (2 μg/ml, Southern Biotechnology Associates) for 2 hours at 37° C. Finally, alkaline phosphatase substrate p-nitrophenyl phosphate (Sigma, St. Louis, Mo.) was added to the plates at 1 mg/ml to visualize positive reactions. OD values were collected using a spectrophotometer (Titertek Multiskan MC, Flow Laboratories, McLean, Va.) at 405 nm wavelength.

IgM (1.3±0.4 mg/ml control versus 5.0±5.0 mg/ml transgenic), IgG$_1$, (1.6±0.8 versus 3.1±0.3), IgG$_{2a}$ (0.28±0.08 versus 0.22±0.8) and IgA (3.4±1.7 versus 3.6±1.5) levels were not significantly different between control littermates and transgenic mice. Therefor, at least on the level of total antibody response, the transgenic mice were not notably immunocompromised.

The pattern of expression of the hCD19 gene in transgenic mice demonstrates that the elements which regulate B cell-specific expression are contained within the transgene and are functional in a mouse genetic background (FIG. 6, 7, 8, 10). Furthermore, regulation of hCD19 expression during B cell development in transgenic mice was similar to that observed in humans, with expression starting at the pre-B cell stage of maturation.

Although the endogenous promoter and enhancer regions of the Ig light and heavy chain genes are also active early in the lymphocyte lineage, expression of the Ig heavy chain promoter unit is not completely B cell-restricted in some transgenic mice (Grosschedl, et al., 1984 Cell, 38, 647–658; Lamers, et al., 1989 Eur. J. Immunol., 19, 459–468; Nussenweig, et al., 1987, Science, 236, 816–819). The κ light chain gene initiates B cell-specific although not B-cell-restricted gene expression, in that κ gene expression was found in kidney cells of one transgenic mouse, and in some T-cell populations (Storb, et al.,1984, Nature, 310, 238–241). Although the κ light chain gene shares no significant homology with 5' flanking sequences of the CD19 gene, the CD19 gene contains sequences similar to the NFκB and µB motifs (Zhou et al., 1992, supra). Binding sites for the B cell-specific activator protein (BSAP)/Pax-5 transcription regulatory factor have also been functionally characterized in the CD19 promoter region (Adams, et al., 1992 Genes & Dev., 6, 1589–1607; Kozmik, et al., 1992, Molec. Cell. Biol., 12, 2662–2672). BSAP/Pax-5 is expressed within the hematopoietic system with equal binding activity in pro-B, pre-B and mature B cells (Barberis, et al., 1990, Genes Dev., 4, 849–859).

In contrast to many other transgenes, there was a positive correlation between the number of hCD19 transgene copies present and the surface expression of hCD19 on mouse B cells with homozygous transgenic mice (FIG. 6). The CD19 regulatory elements provide a model of lineage-specific gene regulation and also provides regulatory element(s) useful for gene therapy since expression of the hCD19 gene was B cell-restricted and relatively independent of insertional effects.

Expression of the human CD19 transgene was completely B cell-restricted and expression of the hCD19 gene product severely altered normal B cell development in the transgenic mice, suggesting that CD19 is an important factor in regulating early B cell development.

Expression of the hCD19 transgene inhibited the development of mouse B lineage cells in direct relation to the quantity of gene product expressed. However, the percentage of $IgM^-B220^{dull}$ pre-B cells in the bone marrow of h19-1 transgenic mice did not change dramatically, indicating that pre-B cell development was not significantly inhibited and that pre-B cell accumulation at this stage of differentiation did not occur (FIGS. 10, 11). In contrast, the number of immature $IgM^+B220^{dull}$ B cells and $B220^{bright}$ $Ig<^+ IgD^+$ mature B cells in the bone marrow of transgenic mice was significantly reduced, suggesting that transgene expression has a significant effect on immature B cell development. Expression of the hCD19 transgene did not completely obstruct normal B cell maturation since mature B cells were found in the circulation and in peripheral lymphoid organs, although at significantly lower frequencies. The frequency of B cells in peripheral blood and spleen of homozygous h19-1 transgenic mice was reduced by 96% and 82%, respectively (FIG. 9). The presence of normal-appearing B cells in blood, secondary lymphoid organs and the peritoneal cavity presumably reflects the peripheral expansion of mature B lymphocytes where normal CD19 function may not be strictly required. However, the effect of the hCD19 transgene was not completely compensated for by the accumulation of peripheral B cells since old mice continued to have a significant deficit in circulating B cell numbers (FIG. 6). Similar results were obtained in most transgenic lines, with the severity of the defect correlating with the level of hCD19 expression (Table 1, FIG. 6). This dose response effect in independent lines of transgenic mice implicates the hCD19 gene product as the direct cause of impaired B cell development rather than an insertional effect.

The defect in B lymphocyte development appears to occur initially in the bone marrow microenvironment since this compartment identifies the first site of skewed B cell development. This suggests that expression of hCD19 by mouse B cells may not alter antigen-dependent signal transduction since the bone marrow is a site of antigen-independent B cell development and the stage of B cell development most profoundly affected is antigen-independent (Rolink and Melchers, 1991, Cell, 66, 1081–1094). The paucity of B cells in bone marrow, blood and tissues does not appear to result from dysregulation of normal B cell activation since h19-1 transgenic mice had normal levels of serum immunoglobulins of all isotypes. Spleen B cells from h19-1 transgenic mice and control littermates were also equivalent in their response to IgM crosslinking as evidenced by their ability to rapidly increase intracellular $Ca^{++}$ levels (FIG. 12). Although the mechanism for hCD19 interference with bone marrow lymphopoiesis in the transgenic mice is unclear, increased turnover of B-lineage cells does not readily account for all of the differences in B cell numbers since cell cycle analysis of pre-B cells and B cells from transgenic mice and control littermates did not reveal significant differences in cellular proliferation. Also, the bone marrow pre-B cell population was approximately normal in number in transgenic mice. The hCD19-induced defect does not appear to result from altering endogenous mCD19 expression since it was not down-regulated by expression of the hCD19 gene as detected by Northern blot analysis. Therefore, CD19 may function in regulating antigen-independent B cell development or survival during the late pre-B cell stage or the period of transition from a pre-B cell into an immature B cell.

Surface Ig and CD19 may share common signal transduction pathways since the prior engagement of either receptor with mAb can ablate the ability of the second receptor to induce changes in $[Ca^{++}]_i$ (Pezzutto et al., 1987 J. Immunol., 138, 2793–2799; Rijkers et al., 1990, Proc. Natl. Acad. Sci. USA, 87, 8766–8770). However, inappropriate activity of CD19 due to increased receptor number did not appear to result in desensitization of other signal transduction pathways in the hCD19 transgenic mice since crosslinking of CD19 or IgM induced a potent change in $[Ca^{++}]_i$ (FIG. 12). Whereas impairment of B cell development was correlated with the number of hCD19 molecules expressed on the cell surface, it is possible that intracellular kinases or other members of the mCD19 complex bind the human molecule and are thereby not available for proper signal transduction through mCD19. This is a possibility since the amino acid sequence homology between mouse and human CD19 is high (Tedder and Isaacs, 1989, supra).

EXAMPLE III

Examples of B-cell deficiencies which lead to gene product deficits normally provided by B-cells, and methods for treating such deficiencies according to the invention are provided below.

1. Diseases Involving B-cell Immunodeficiency.

Immunodeficiency disease results from the absence, or failure of normal function, of one or more elements of the immune system. Specific immunodeficiency diseases involve abnormalities of T or B cells, the cells of the adaptive immune system. Primary immunodeficiency diseases are due to intrinsic defects in cells of the immune system and are for the more part genetically determined. Secondary immunodeficiency diseases result from extrinsic factors, such as drugs, irradiation, malnutrition or infection.

Immunodeficiency diseases cause increased susceptibility to infection in patients. The infections encountered in immunodeficient patients fall, broadly, into two categories. Patients with defects in immunoglobulins or complement proteins or phagocytes are very susceptible to recurrent infections with encapsulated bacteria, such as *Hemophilus* influenzae, Streptococcus pneumoniae, Staphylococcus aureus, etc. Patients with defects in cell-mediated immunity, i.e., T cells, are susceptible to overwhelming, even lethal, infections with microorganisms that are ubiquitous in the environment and to which normal people rapidly develop resistance. Such infections are called opportunistic infections; opportunistic microorganisms include yeast and common viruses such as chickenpox.

The primary B cell deficiencies include X-linked agammaglobulinemia, IgA deficiency, IgG subclass deficiency, immunodeficiency with increased IgM, common variable immunodeficiency, and transient hypogammaglobulinaemia of infancy. The range of B cell deficiencies varies from a delayed maturation of normal immunoglobulin production, through single isotype deficiencies to X-linked agammagloblinaemia, where affected male children have no B cells and no serum immunoglobulins. Patients with these defects have recurrent pyogenic infection such as pneumonia, otitis media and sinusitis. If untreated, they develop severe obstructive lung disease (bronchiectasis) from recurrent pneumonia, which destroys the elasticity of the airways.

The model B cell deficiency is X-linked agammaglobulinemia. Affected males have no B cells in their blood or lymphoid tissue; consequently their lymph nodes are very small and their tonsils absent. Their serum contains no IgA, IgM, IgD, or IgE and only small amounts of IgG. After maternal IgG is exhausted in the newborn after the first 6–12 months of life, these affected males develop recurrent pyogenic infections, and must be infused intravenously with large doses of gamma-globulin to remain healthy.

The X-LA gene is on the long arm of the X-chromosome. This is the site of many other immunodeficiency diseases; the localization of these genes facilitates prenatal diagnosis. Bone marrow of males with X-LA contains normal numbers of pre-B cells which, for unknown reasons, cannot mature into B cells. The gene for X-LA is provided in Tzukada et al., 1993, Cell 72: 279–290, hereby incorporated by reference. Other X-linked immunodeficiencies include X-linked chronic granulomatous disease, Wiskott-Aldrich syndrome, X-linked severe combined immunodeficiency, and X-linked immunodeficiency with increased IgM.

IgA deficiency is the most common immunodeficiency. One in 700 Caucasians have the defect, but it is not found, or is found only rarely, in other ethnic groups. People with IgA deficiency tend to develop immune-complex disease (Type II hypersensitivity). About 20% of IgA-deficient individuals also lack IgG2 and IgG4, and are very susceptible to pyogenic infections. In humans, most antibodies to the capsular polysaccharides of pyogenic bacteria are in the IgG2 subclass. A deficiency in IgG2 alone therefore results in recurrent pyogenic infections as well. For reasons that are unclear, individuals with deficiency of IgG3 only are also susceptible to recurrent infections. These class and subclass deficiencies result from failure in terminal differentiation of B cells.

Another immunodeficiency results in patients who are IgG- and IgA-deficient but synthesize large amounts of polyclonal IgM. They are susceptible to pyogenic infections and should be treated with intravenous gamma-globulin. They tend to form IgM autoantibodies to neutrophils, platelets and other elements of the blood, as well as to tissue antigens, thereby adding the complexities of autoimmune disease to the immunodeficiency. The tissues, particularly of the gastrointestinal tract, become infiltrated with IgM-producing cells.

Individuals with common variable immunodeficiency (CVID) have acquired agammaglobulinemia in the second or third decade of life, or later. Both males and females are equally affects and the cause of the acquisition of agammaglobulinemia is generally not known, but may follow infection with viruses such as Epstein-Barr virus (EBV), which causes infections mononucleosis. Patients with CVID, like males with X-LA, are very susceptible to pyogenic organisms and to the intestinal protozoan, Giardia lamblia, which causes severe diarrhoea. Most patients (80%) with CVID are treated with intravenous gamma-globulin to protect against recurrent pyogenic infections. Many patients with CVID develop autoimmune diseases, most prominently pernicious anaemia. CVID is not hereditary, but is commonly associated with the MHC haplotypes HLA-B8 and HLA-DR3.

Figure 2:
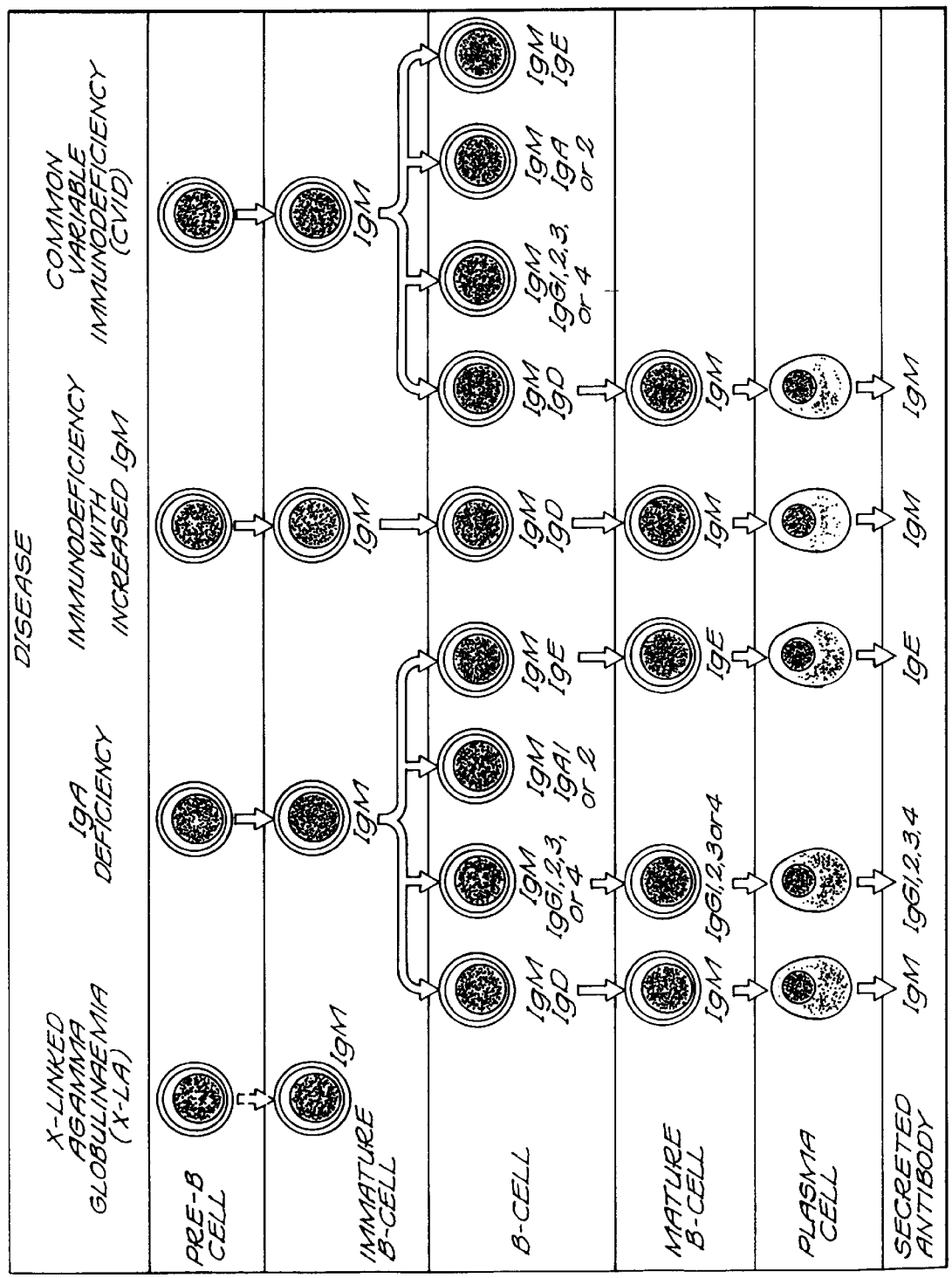
FIG. 2 is a chart of the prior art showing B cell maturation in X-linked immunodeficiencies.
Figure 5B:
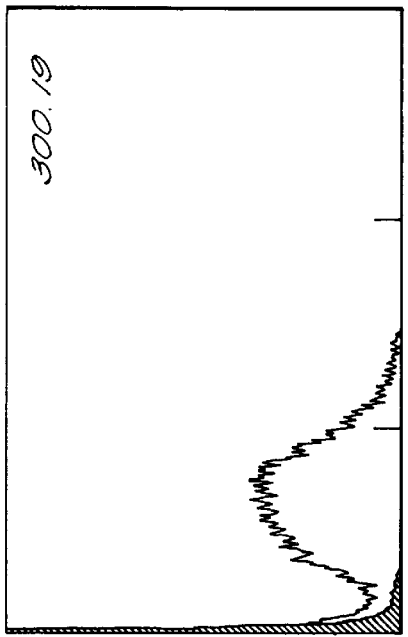
FIG. 5 is a series of histograms showing the relative numbers of cells staining positive with an anti-CD19 antibody in different B and T cell lines.
Figure 5D:
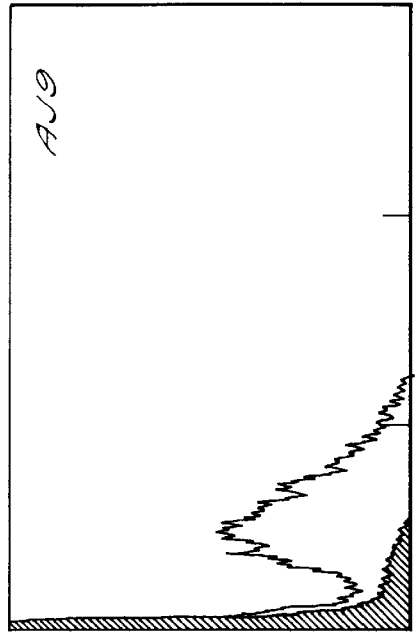
Figure 5A:
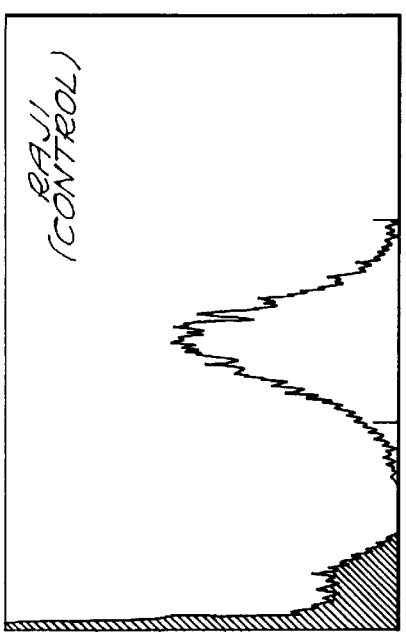
Figure 5C:
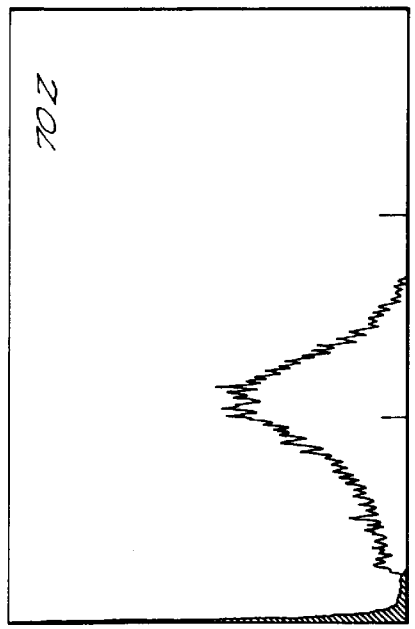
Figure 5F:
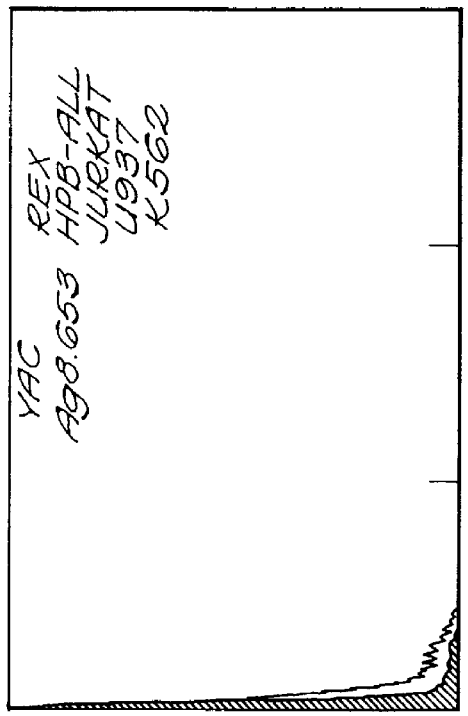
Figure 5E:
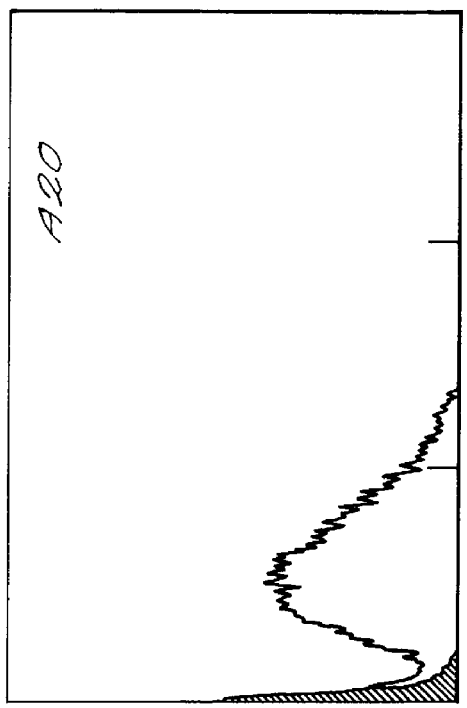

FIG. 2 shows B cell maturation in X-linked immunodeficiencies.

2. Preparing Constructs Useful for Treating B-cell Deficiencies.

Genes which may be used in constructs to treat B cell disorders or to produce B cell proteins may include, e.g., the X-LA gene, any of the Ig genes, the XID gene, or any other gene of interest. Upon cloning of other genes containing defects resulting in immunodeficiencies, one of skill in the art would be able to link the coding regions of such genes to the CD19 B-lineage-restricted regulatory elements, in order to express such genes in a B-cell-restricted manner.

In vivo production of a B cell product to restore the product deficiency in immunodeficiencies based on B cell disorders can be accomplished as follows.

DNA may be isolated by conventional techniques, e.g., as described in Maniatis et al., Molecular Cloning, Cold Spring Harbor Laboratory, Cold Spring Harbor (1982). Restriction endonucleases are used according to the suppliers, instructions (New England Biolabs, Beverly, Mass.) to perform digestions, and the fragments may be recovered, e.g., by low-melt agarose gels as described by Weislander, L., Anal. Biochem. 98, 305 (1979). Nucleotide sequences are determined using the methods of Sanger et al., 1977, Proc. Nat. Acad. Sci. 74: 5463–5467.

A construct containing B-lineage regulatory elements and a gene encoding the product to be restored may be transfected into susceptible mammalian cells. The B-lineage regulatory elements/heterologous gene construct may be transfected, as described herein. The number of gene copies to be transfected will be that number which is sufficient to transfect susceptible mammalian cells such that the heterologous gene product is produced therefrom. The heterologous gene may also be introduced into the mammalian system using DNA constructs for retrovirus packaging cell lines as described in U.S. Pat. No. 4,861,719, incorporated herein by reference. Briefly, a cell line containing a DNA construct such as pPAM3 (ATCC No. 40234) is used to transmit high titers of retroviral vectors which carry the heterologous gene. An example of such a cell line is PA317 (ATCC No. CLR 9078). Useful DNA constructs such as PAM3 are constructed by deleting all of the cis-acting elements except for the tRNA binding site from the genome of a replication-competent retrovirus. The particular cis-acting elements which are deleted are: the packaging signal, the site for initiation of second strand DNA synthesis, the site required for translation of reverse transcriptase during first strand DNA synthesis, and the provirus integration signal. The retrovirus vectors produced by PA317 cells are capable of infecting a variety of hosts, including human, mouse, rat, cat, and dog cells. Hemopoietic progenitor cells from human bone marrow and mouse embryo cells have been infected by retroviral vectors secreted from PA317 cells. The vector titer from the PA317 cells is very high (up to $10^7$ colony forming units/ml), and therefore, these cells are useful in mammalian gene therapy.

As with most diseases involving immunodeficiencies, where there may be no established dosage of the deficient product. The optimal dose is determined empirically for each patient. The optimal dose is that which produces maximal improvement with tolerated side effects.

OTHER EMBODIMENTS

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and scope of the appended claims.

I claim:

1. A mouse having in its germline a gene encoding human CD19 operatively linked to regulatory elements that direct expression specifically in the B cell lineage, wherein said human CD19 gene is expressed in the B cell lineage of said mouse, resulting in said mouse having fewer B220 cells than a normal mouse.

* * * * *

UNITED STATES PATENT AND TRADEMARK OFFICE
CERTIFICATE OF CORRECTION

PATENT NO : 5,831,142
DATED : November 3, 1998
INVENTOR(S): Thomas F. Tedder

It is certified that error appears in the above-identified patent and that said Letters Patent is hereby corrected as shown below:

Column 3, line 64, "A chains" should read --$\mu$ chains--.

Column 4, line 5, "p chains" should read --$\mu$ chains--.

Column 4, line 37, "$M^r$," should read --$M_r$--.

Column 4, line 63, "$[Ca^{++}]_i$" should read --$[Ca^{++}]_i$--.

Column 5, line 26, "Jan. 7, 1997" should read --Jan. 7, 1994--.

Signed and Sealed this

Sixteenth Day of November, 1999

Attest:

Q. TODD DICKINSON

Attesting Officer

Acting Commissioner of Patents and Trademarks